United States Patent
Das et al.

(10) Patent No.: US 11,933,727 B2
(45) Date of Patent: Mar. 19, 2024

(54) COMPUTER-IMPLEMENTED APPARATUS AND METHOD FOR ANALYZING MILK

(71) Applicant: Labby Inc., Cambridge, MA (US)

(72) Inventors: Anshuman Das, Brighton, MA (US); Julia Kang Somerdin, Cambridge, MA (US)

(73) Assignee: Labby Inc., Cambridge, MA (US)

( * ) Notice: Subject to any disclaimer, the term of this patent is extended or adjusted under 35 U.S.C. 154(b) by 0 days.

(21) Appl. No.: 18/164,916

(22) Filed: Feb. 6, 2023

(65) Prior Publication Data
US 2023/0251196 A1 Aug. 10, 2023

Related U.S. Application Data

(60) Provisional application No. 63/307,461, filed on Feb. 7, 2022.

(51) Int. Cl.
*G01N 21/64* (2006.01)
*G01N 33/04* (2006.01)
*G06N 20/00* (2019.01)

(52) U.S. Cl.
CPC ......... *G01N 21/6428* (2013.01); *G01N 33/04* (2013.01); *G06N 20/00* (2019.01); *G01N 2021/6441* (2013.01)

(58) Field of Classification Search
None
See application file for complete search history.

(56) References Cited

U.S. PATENT DOCUMENTS

| 6,535,753 | B1* | 3/2003 | Raskas | A61B 5/6825 600/476 |
| 8,173,970 | B2* | 5/2012 | Inbar | G01V 5/0075 250/390.07 |
| 9,029,803 | B2* | 5/2015 | Kishima | G01N 21/6428 250/459.1 |
| 10,352,847 | B2* | 7/2019 | Das | G01N 21/80 |
| 11,156,554 | B2* | 10/2021 | Waanders | G01N 21/6486 |
| 11,156,556 | B1 | 10/2021 | Multari et al. | |

(Continued)

FOREIGN PATENT DOCUMENTS

| WO | 2010/146199 A2 | 12/2010 |
| WO | 2016/034189 A1 | 3/2016 |

OTHER PUBLICATIONS

Gareth James et al., "An Introduction to Statistical Learning, with Applications in R", Springer Science + Business Media, NY, 2013, 438 pages.

(Continued)

*Primary Examiner* — David P Porta
*Assistant Examiner* — Djura Malevic
(74) *Attorney, Agent, or Firm* — Sunstein LLP

(57) ABSTRACT

A computer-implemented system for determining an analyte in milk is provided. The system first causes irradiation of the sample with light in a plurality of discrete spectral bands. The spectral bands can be selected based on phenomenon of specific analytes. The irradiation causes a fluorescent response in the milk, which is received by light sensors and converted into digitized spectral data. The digitized spectral data is then transmitted to a machine learning system which can determine the concentration of analytes and produce an output indicative of said concentration.

29 Claims, 25 Drawing Sheets

(56) References Cited

U.S. PATENT DOCUMENTS

| | | | | |
|---|---|---|---|---|
| 11,193,894 | B2* | 12/2021 | Waanders | G01N 21/94 |
| 11,262,298 | B2* | 3/2022 | Hodel | G01N 21/3577 |
| 11,635,380 | B2* | 4/2023 | Qiu | G01N 21/278 |
| | | | | 250/459.1 |
| 2004/0179194 | A1 | 9/2004 | Schmilovitch et al. | |
| 2005/0107676 | A1* | 5/2005 | Acosta | A61B 5/1455 |
| | | | | 600/316 |
| 2009/0255473 | A1 | 10/2009 | Katz et al. | |
| 2013/0089876 | A1* | 4/2013 | Sadik | G01N 33/566 |
| | | | | 422/69 |
| 2015/0177147 | A1 | 6/2015 | Mangan et al. | |
| 2016/0100777 | A1* | 4/2016 | Bechtel | A61B 5/14532 |
| | | | | 600/316 |
| 2016/0238520 | A1 | 8/2016 | Broutin | |
| 2017/0045441 | A1* | 2/2017 | Nciri | G01J 3/10 |
| 2017/0176255 | A1* | 6/2017 | Nciri | G01J 3/0224 |
| 2018/0372623 | A1* | 12/2018 | Das | G01N 15/00 |
| 2019/0293620 | A1* | 9/2019 | Farkas | G01N 21/6456 |

OTHER PUBLICATIONS

"How do you milk a cow using milking machines?", Undeniably Dairy, Sep. 14, 2016 (5 pp), https://www.usdairy.com/news-articles/how-do-you-milk-a-cow.

"Milking, milk production hygiene and udder health", FAO Animal Production and Health Paper 78, Section 2: Milking Machines and Equipments, Food and Agriculture Organization of the United Nations, Rome, 1989 (25 pp), https://www.fao.org/3/T0218E/T0218E02.htm.

European Patent Office, International Searching Authority, Notification of Transmittal of the International Search Report and the Written Opinion of the International Searching Authority, or the Declaration, dated May 31, 2023 in International Patent Application No. PCT/US2023/062032, 18 pages.

* cited by examiner

Fig. 17E

Cow List

Mastitis Watch List | Mastitis High Alert | Ketosis Watch | Reserved

- 1001 — Health Check
- 1002 — Health Check
- 1003 — Health Check

Fig. 17F

Individual Cow Info

1003

- 0.0% Fat
- 0.0% Protein
- 0k/ml SCC

SCC Weekly Deviation

01/16/22 to 01/17/22

Cow Trend

Fat% | Protein% | SCC

| Molecules | Excitation (nm) | Emission (nm) | Target Analyte |
|---|---|---|---|
| Immune antibodies | 410 | 570 | Cells |
| Nicotinamide adenine dinucleotide (NADH) | 340 | 450 | Cells |
| Lipo-pigments | 350 | 600 | Cells |
| Flavins | 450 | 550 | Fat |
| Lactoferrin | 450 | 560 | Cells |
| Porphyrins | 410 | 630 | Blood, Cells, Chlorophyll |
| Estrogen | 350 | 530 | Hormones |
| Tryptophan | 280 | 330 | Protein, Lactose |

COMPUTER-IMPLEMENTED APPARATUS AND METHOD FOR ANALYZING MILK

PRIORITY

The present application claims the benefit of provisional application Ser. No. 63/307,461, filed Feb. 7, 2022, which is hereby incorporated herein by reference, in its entirety.

TECHNICAL FIELD

The present invention relates to spectrographic analysis devices and methods, and more particularly to devices and methods for analyzing milk.

SUMMARY OF THE EMBODIMENTS

In accordance with one embodiment of the invention, there is provided a computer implemented method of analyzing a milk sample. In this embodiment, the method uses a processor executing instructions to establish computer processes. These processes include:

causing irradiation of the sample with light in a plurality of discrete spectral bands, lying in a range from near-infrared through ultraviolet, to cause production of a fluorescence response;

receiving, from an analog to digital converter coupled to a set of light sensors, digitized spectral data that includes first data characterizing the fluorescence response; and transmitting the digitized spectral data to a machine learning system, the system having been trained to determine concentration in the sample of a set of analytes selected from the group consisting of somatic cells, fat, protein, lactose, antibiotics, pathogens, hormones, and combinations thereof and to produce a concentration data output.

In this embodiment, each one of the discrete spectral bands has been selected on the basis of a fluorescence phenomenon of a corresponding one of the analytes.

Optionally, causing irradiation of the sample includes causing irradiation of the sample sequentially in each one of the plurality of discrete spectral bands. Also optionally, the discrete spectral band selected for the corresponding one of the analytes is a discrete spectral band selected on the basis of a fluorescence phenomenon of a biomarker identified as a proxy for the corresponding one of the analytes.

In further related embodiments, the corresponding one of the analytes is cells and the identified biomarker is immune antibodies, for which the irradiation is caused in a spectral band including 410 nm and the fluorescence response is in a spectral band at 570 nm. Alternatively, the corresponding one of the analytes is cells and the identified biomarker is nicotinamide adenine dinucleotide, for which the irradiation is caused in a spectral band including 340 nm and the fluorescence response is in a spectral band including 450 nm. Also alternatively, the corresponding one of the analytes is cells and the identified biomarker is lipo-pigments, for which the irradiation is caused in a spectral band including 350 nm and the fluorescence response is in a spectral band including 600 nm. As a further alternative, the corresponding one of the analytes is fat and the identified biomarker is flavins, for which the irradiation is caused in a spectral band including 450 nm and the fluorescence response is in a spectral band including 550 nm. As another alternative, the corresponding one of the analytes is cells and the identified biomarker is lacto-ferrin, for which the irradiation is caused in a spectral band including 450 nm and the fluorescence response is in a spectral band including 560 nm. As yet another alternative, the corresponding one of the analytes is selected from the group consisting of blood, cells, chlorophyll and combinations thereof and the identified biomarker is porphyrins, for which the irradiation is caused in a spectral band including 410 nm and the fluorescence response is in a spectral band including 630 nm. In another alternative, the corresponding one of the analytes is hormones and the identified biomarker is estrogens, for which the irradiation is caused in a spectral band including 350 nm and the fluorescence response is in a spectral band including 530 nm. Also alternatively, the corresponding one of the analytes is selected from the group consisting of protein and lactose and the identified biomarker is tryptophan, for which the irradiation is caused in a spectral band including 280 nm and the fluorescence response is in a spectral band including 330 nm.

In another related embodiment, causing irradiation of the sample further includes causing irradiation to cause production of a transmitted light response and the digitized spectral data include second data characterizing the transmitted light response.

In another embodiment of the present invention, there is provided a computer-implemented system for analyzing a milk sample. In this embodiment, the system includes:

a receptacle configured to removably receive the milk sample;

a light source configured to irradiate the sample at a plurality of discrete spectral bands, lying in a range from near-infrared through ultraviolet to cause production of a fluorescence response;

a light detector and an analog-to-digital converter coupled thereto providing a digitized spectral data output that includes first data characterizing the fluorescence response; and a machine learning system coupled to the digitized spectral data output, the machine learning system having been trained to determine concentration in the sample of a set of analytes selected from the group consisting of somatic cells, fat, protein, lactose, antibiotics, hormones, and combinations thereof and to produce a concentration data output.

In this embodiment, each one of the discrete spectral bands has been selected on the basis of a fluorescence phenomenon of a corresponding one of the analytes.

Optionally, causing irradiation of the sample includes causing irradiation of the sample sequentially in each one of the plurality of discrete spectral bands. Also optionally, the discrete spectral band selected for the corresponding one of the analytes is a discrete spectral band selected on the basis of a fluorescence phenomenon of a biomarker identified as a proxy for the corresponding one of the analytes.

In further related embodiments, the corresponding one of the analytes is cells and the identified biomarker is immune antibodies, for which the irradiation is caused in a spectral band including 410 nm and the fluorescence response is in a spectral band at 570 nm. Alternatively, the corresponding one of the analytes is cells and the identified biomarker is nicotinamide adenine dinucleotide, for which the irradiation is caused in a spectral band including 340 nm and the fluorescence response is in a spectral band including 450 nm. Alternatively, the corresponding one of the analytes is cells and the identified biomarker is lipo-pigments, for which the irradiation is caused in a spectral band including 350 nm and the fluorescence response is in a spectral band including 600 nm. Also alternatively, the corresponding one of the analytes is fat and the identified biomarker is flavins, for which the irradiation is caused in a spectral band including 450 nm and the fluorescence response is in a spectral band including 550 nm. In another alternative, the corresponding one of the analytes is cells and the identified biomarker is lacto-ferrin, for which the irradiation is caused in a spectral band including 450 nm and the fluorescence response is in a spectral band including 560 nm. As a further alternative, the corresponding one of the analytes is selected from the group consisting of blood, cells, chlorophyll and combinations thereof and the identified biomarker is porphyrins, for which the irradiation is caused in a spectral band including 410 nm and the fluorescence response is in a spectral band including 630 nm. In another alternative, the corresponding one of the analytes is hormones and the identified biomarker is estrogens, for which the irradiation is caused in a spectral band including 350 nm and the fluorescence response is in a spectral band including 530 nm. In yet another alternative, the corresponding one of the analytes is selected from the group consisting of protein and lactose and the identified biomarker is tryptophan, for which the irradiation is caused in a spectral band including 280 nm and the fluorescence response is in a spectral band including 330 nm.

In another related embodiment, the light source is further configured to cause production of a transmitted light response and the digitized spectral data include second data characterizing the transmitted light response. Alternatively or in addition, the receptacle is configured to receive and analyze the milk sample from an inline system. Also alternatively or in addition, the computer-implemented system is configured to receive and analyze a series of milk samples over a succession of test frames.

In another embodiment, the invention provides a method for estimating future milk yield of a cow. This method uses a processor executing instructions to establish computer processes, and the processes include:
    obtaining data concerning the cow relating to parameters selected from the group consisting of genetic data and historical time series data, including milk yield, milk composition, days in milk, lactation stage, number of lactations, feed formula, geographic and weather;
    normalizing the obtained data; and
    applying a machine learning model to the normalized and obtained data to estimate future milk yield of the cow.

In yet another embodiment, the invention provides a method for estimating future health status of a cow. The method uses a processor executing instructions to establish computer processes including:
    obtaining data concerning the cow relating to parameters selected from the group consisting of genetic data and historical time series data, including milk yield, milk composition, days in milk, lactation stage, number of lactations, feed formula, geographic and weather;
    normalizing the obtained data; and
    applying a machine learning model to the normalized obtained data to estimate future health status of the cow.

In another embodiment, the invention provides a method for automatically determining milk yield and milk composition from a cow. In this embodiment, the cow is coupled to an inline milking system, in a manner wherein milk from the cow is in a discrete flow path of the inline milking system. Also in this embodiment, the cow has an identifier. The method includes:
    diverting a proportion of the cow's milk in the flow path;
    storing the diverted milk in a milk buffer vial until a milking completion time when milk ceases to flow into the buffer vial;
    determining the volume of milk in the milk buffer vial at the milking completion time;
    using the determined volume of milk to calculate the milk yield using the proportion;
    analyzing the milk in the milk buffer vial using the method of claim 1 to produce a milk analysis; and
    storing the milk yield and the milk analysis in a database in association with the cow's identifier.

In another embodiment of the invention, there is provided a computer-implemented method of calibrating a milk analysis device, the method using a processor executing instructions to establish computer processes comprising:
    causing irradiation of each one of a set of milk samples by the milk analysis device to cause production of a first set of fluorescence responses, each fluorescence response of the first set of fluorescence responses being associated with a corresponding sample of the set of milk samples;
    causing irradiation of each one of the set of milk samples by a benchmarking device to cause production of a second set of fluorescence responses, each fluorescence response of the second set of fluorescence responses being associated with a corresponding sample of the set of milk samples;
    receiving, from the milk analysis device, a first set of digitized spectral data, each one of the first set of digitized spectral data characterizing a corresponding one of the first set of fluorescence responses;
    receiving, from the benchmarking device, a second set of digitized spectral data, each one of the second set of digitized spectral data characterizing a corresponding one of the second set of fluorescence responses; and
    comparing the first and second sets of digitized spectral data ratiometrically to determine a calibration factor for the milk analysis device.

In yet another embodiment, the invention provides a method for maintaining the calibration of a milk analysis device, the method comprising:
    performing a blank measurement on the device in the absence of milk;
    retrieving a previously recorded blank measurement performed on the device;
    comparing the blank measurements to determine a compensation factor; and
    adjusting the exposure time and light source brightness by the compensation factor.

BRIEF DESCRIPTION OF THE DRAWINGS

The foregoing features of embodiments will be more readily understood by reference to the following detailed description, taken with reference to the accompanying drawings, in which:

FIG. 17A through FIG. 17I are representations of successive displays in a smartphone application showing how a user can initiate milk testing on a handheld device, and evaluate a cow or farm's performance in accordance with an embodiment of the present invention;

DETAILED DESCRIPTION OF SPECIFIC EMBODIMENTS

Definitions. As used in this description and the accompanying claims, the following terms shall have the meanings indicated, unless the context otherwise requires:

A "computer process" is the performance of a described function in a computer system using computer hardware (such as a processor, field-programmable gate array or other electronic combinatorial logic, or similar device), which may be operating under control of software or firmware or a combination of any of these or operating outside control of any of the foregoing. All or part of the described function may be performed by active or passive electronic components, such as transistors or resistors. In using the term "computer process" we do not necessarily require a schedulable entity, or operation of a computer program or a part thereof, although, in some embodiments, a computer process may be implemented by such a schedulable entity, or operation of a computer program or a part thereof. Furthermore, unless the context otherwise requires, a "process" may be implemented using more than one processor or more than one (single- or multi-processor) computer.

A "set" includes at least one member.

A method, device, or system is "computer-implemented," if it utilizes a set of computer processes established by execution by a processor of instructions.

Figure 1:
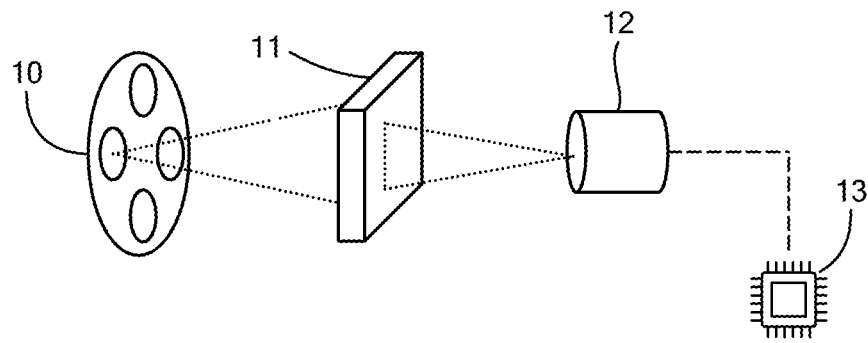
FIG. 1 is a schematic diagram showing components of a fluid analyzer in accordance with an embodiment of the present invention.

FIG. 1 is a schematic diagram showing components of a fluid analyzer in accordance with an embodiment of the present invention. This fluid analyzer includes a light source 10, which is used to illuminate a sample 11, fluorescence and transmitted light from which is read by detector 12. The output of detector 12 is fed to a microprocessor 13 for processing in a manner described hereinbelow.

Figure 2:
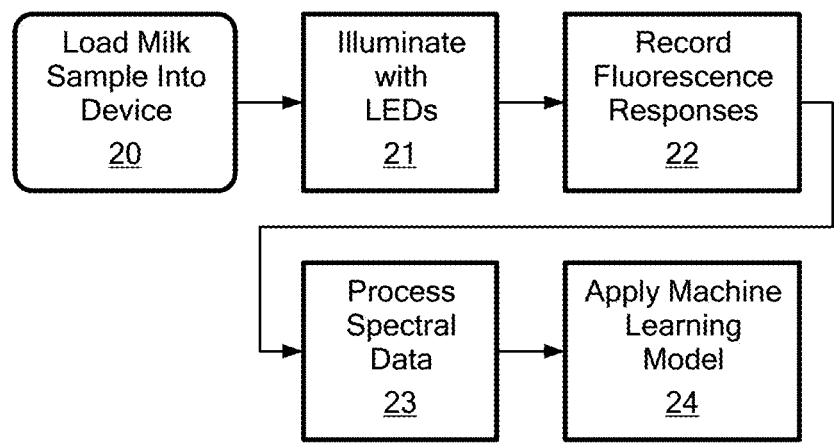
FIG. 2 is a block diagram showing processes by which fluorescence measurements are obtained and used to estimate milk composition in accordance with an embodiment of the present invention.

FIG. 2 is a block diagram showing processes by which fluorescence measurements are obtained and used to estimate milk composition in accordance with an embodiment of the present invention. In process 20, a milk sample is loaded into the fluid analyzer of FIG. 1. In process 21, the milk sample is illuminated using the light source 10 of FIG. 1. In process 22, the responses (which may be fluorescence or transmitted light, or both) from the sample 11 are measured by detector 12. The output from detector 12 is fed to the microprocessor 13 of FIG. 1, which transmits the data to a server system. In process 23, the server system processes the spectral data and, in process 24, applies a machine learning model, to arrive at an estimate of milk composition.

Machine learning models figure largely in this patent application. We use machine learning regression models, namely, such models that support vector regression and artificial neural networks, to estimate (among other things) the concentration of milk analytes based on processed spectral data. Exemplary software packages used in this context include NumPy (see https://numpy.org), Scikit-learn (Sklearn) (see https://scikit-learn.org/stable/index.html), TensorFlow (see https://www.tensorflow.org), and Keras (see https://keras.io), which are configured for use in the Python environment.

Figure 3:
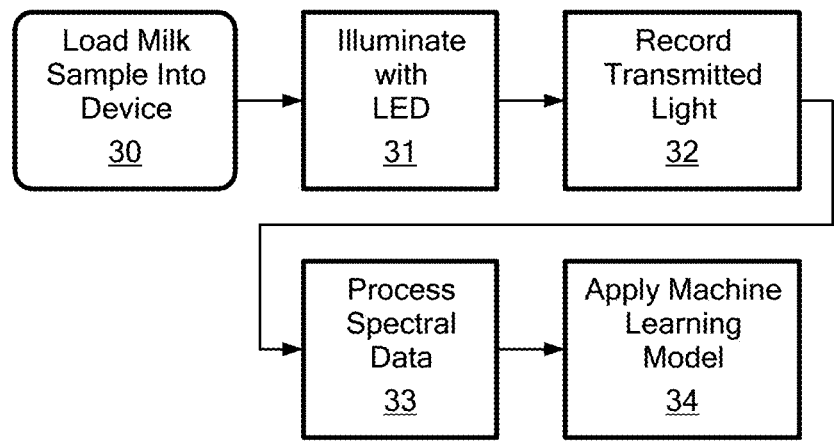
FIG. 3 is a block diagram showing processes by which transmitted light measurements are obtained and used to estimate milk composition in accordance with an embodiment of the present invention.

FIG. 3 is a block diagram showing processes by which transmitted light measurements are obtained and used to estimate milk composition in accordance with an embodiment of the present invention. In process 30, a milk sample is loaded into the fluid analyzer of FIG. 1. In process 31, the milk sample is illuminated using the light source 10 of FIG. 1. In process 32, the transmitted light from the sample 11 is measured by detector 12. The output from detector 12 is fed to the microprocessor 13 of FIG. 1, which transmits the data to a server system. In process 33, the server system processes the spectral data and, in process 34, applies a machine learning model, to arrive at an estimate of milk composition.

Figure 4:
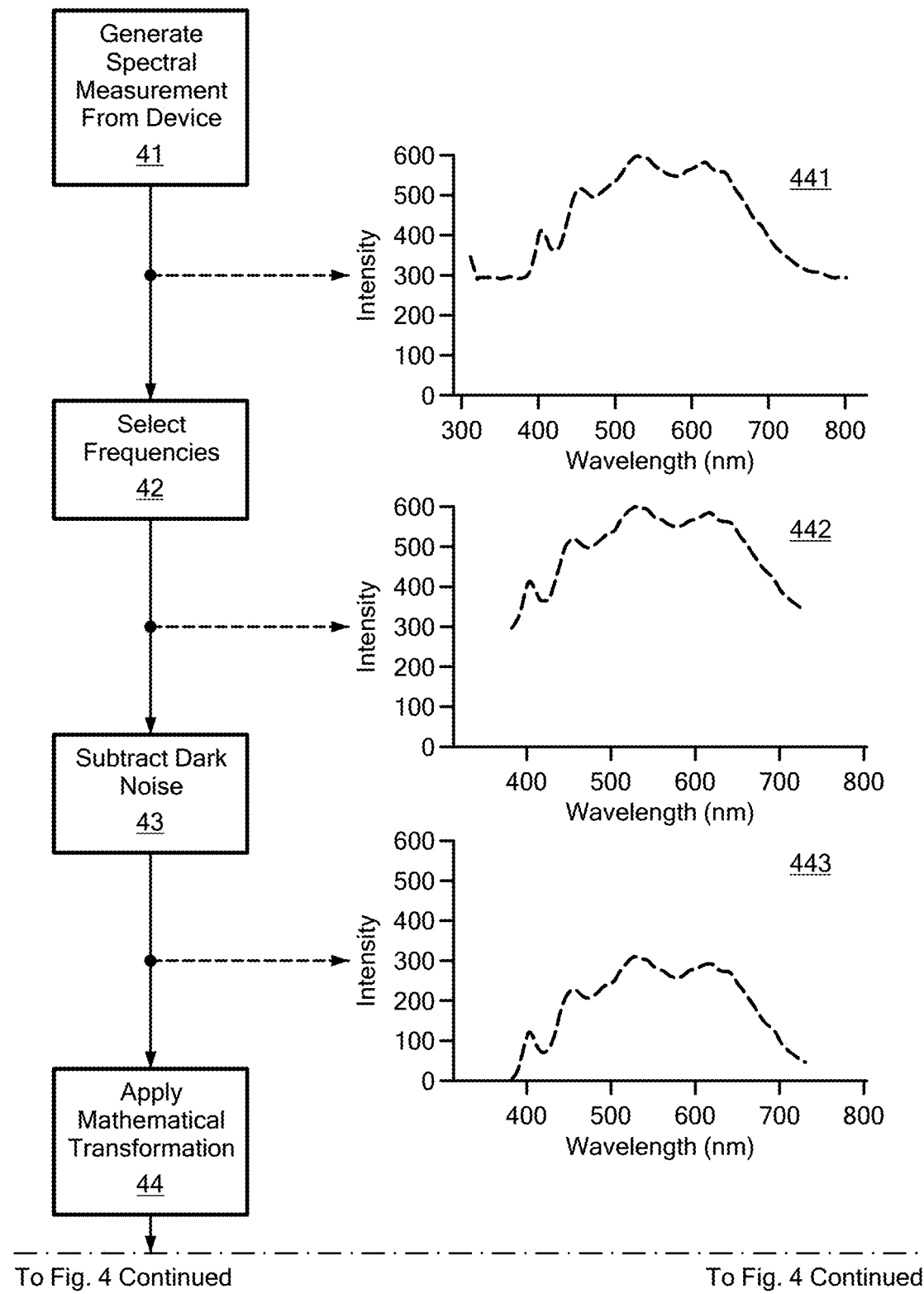
FIG. 4 is a flow diagram showing processes by which spectral data is processed (with corresponding spectral plots at each stage) in accordance with an embodiment of the present invention.
Figure 4:
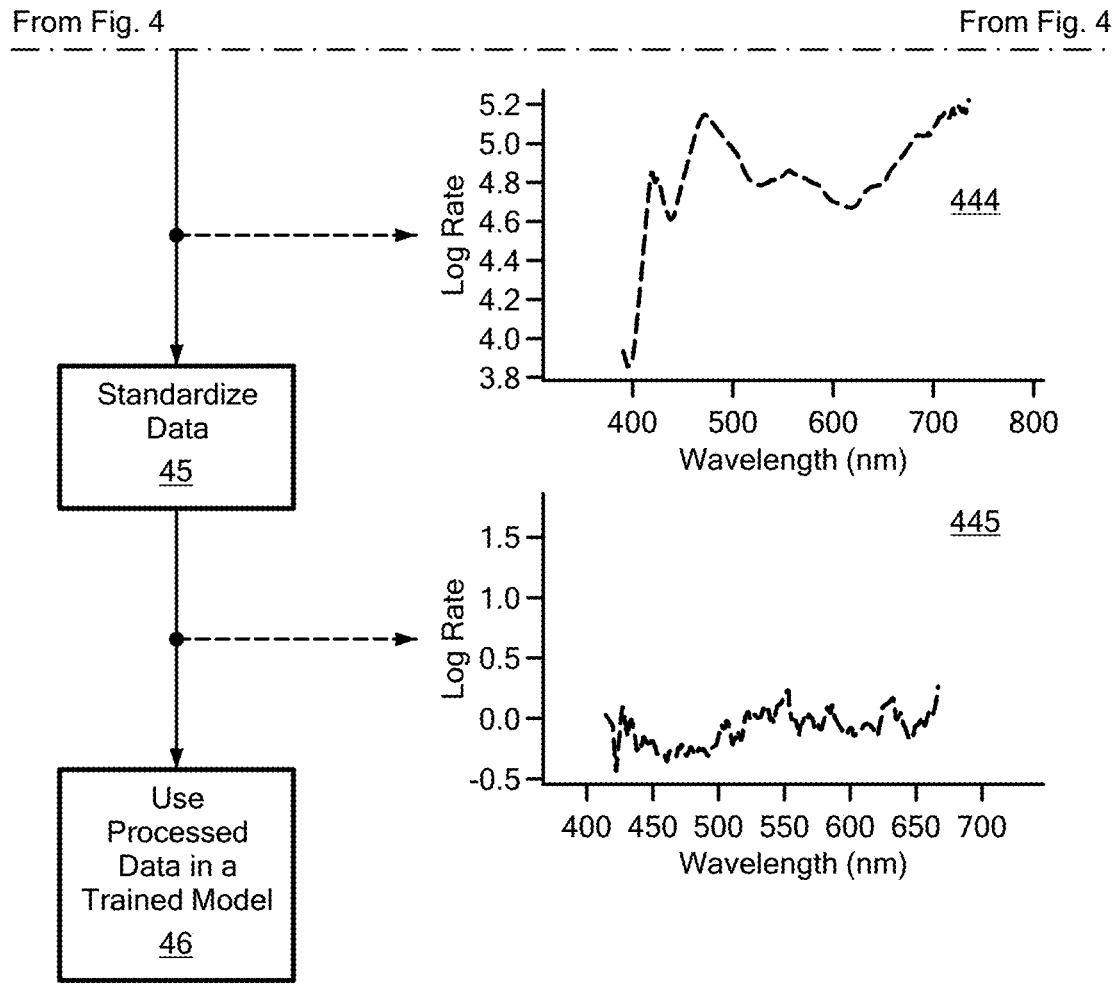

FIG. 4 is a flow diagram showing processes by which spectral data is processed (with corresponding spectral plots at each stage) in accordance with an embodiment of the present invention. In process 41, spectral measurements of a milk sample are generated from a device in accordance with FIG. 1, resulting in spectral response 441. In process 42, wavelengths of interest of the spectral response 441 are selected, resulting in spectral response 442. In process 43, the dark background (namely, the detector output in the absence of illumination) is subtracted from the spectral response 442, resulting in spectral response 443. In process 44, Beer-Lambert law is applied to the subtracted spectral response 443, resulting in spectral response 444. In process 45, the transformed spectral response 444 is normalized (namely, subtracting a mean, and dividing by a standard deviation), resulting in spectral response 445. In process 46, a trained machine learning model is applied to the processed spectral response.

Figure 5:
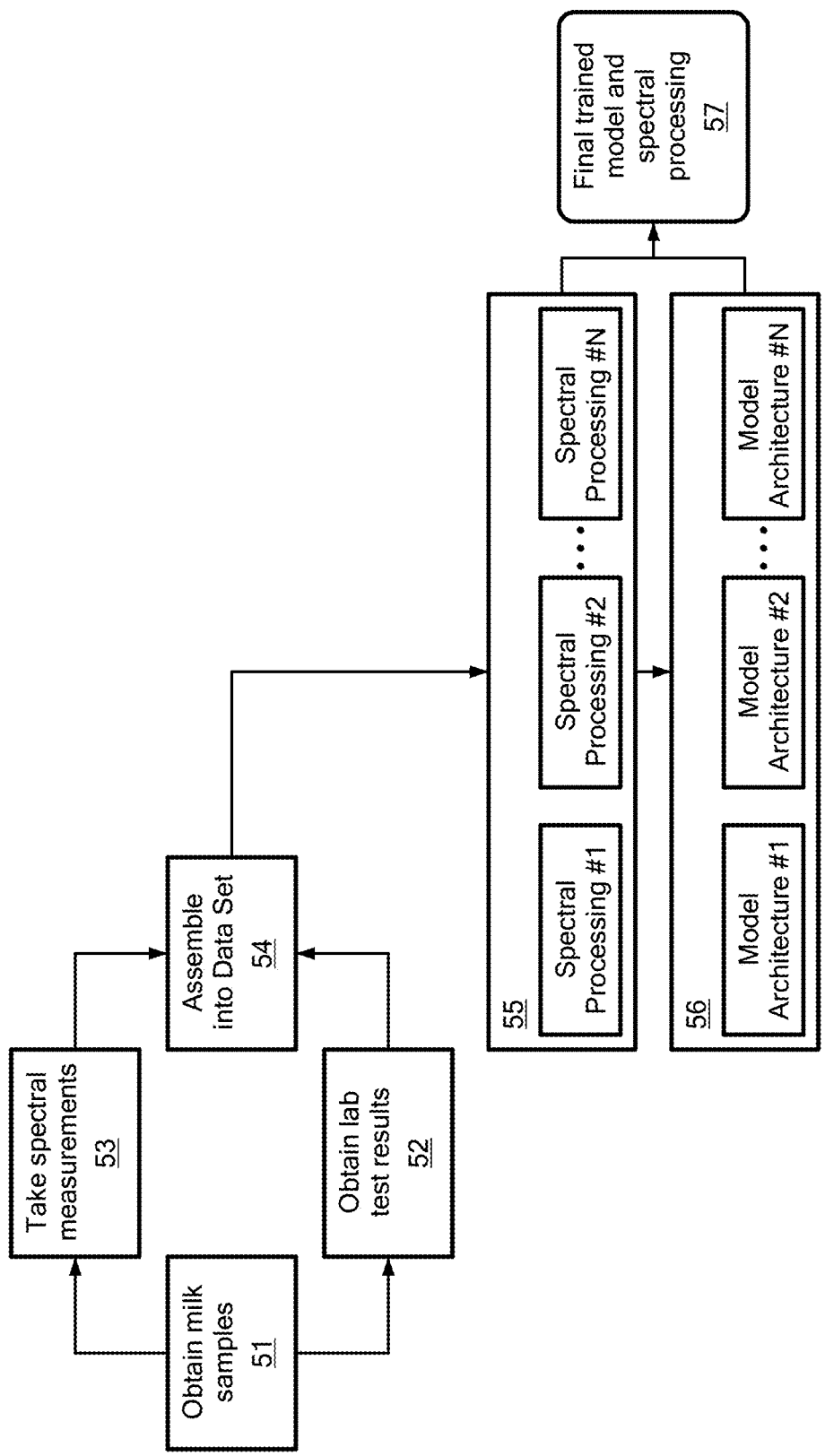
FIG. 5 is a flow diagram showing processes by which machine learning models are trained to estimate milk composition from a spectrum with an embodiment of the present invention.

FIG. 5 is a flow diagram showing processes by which machine learning models are trained to estimate milk composition from a spectral response with an embodiment of the present invention. In process 51, milk samples are collected. In process 52, lab tests are performed on the milk sample to obtain its concentration of components relevant to the training. In process 53, spectral measurements of milk samples are generated using the process of FIG. 2 or FIG. 3, with a device described in FIG. 1. In process 54, the composition information is paired with corresponding spectral data. In process 55, different spectral processing methods are applied to the training data. In process 56, different network architectures are applied to the processed spectral data, and optimized to estimate milk components. In process 57, the best combination of processing and architecture is selected based on their accuracy in estimating milk composition.

Figure 6:
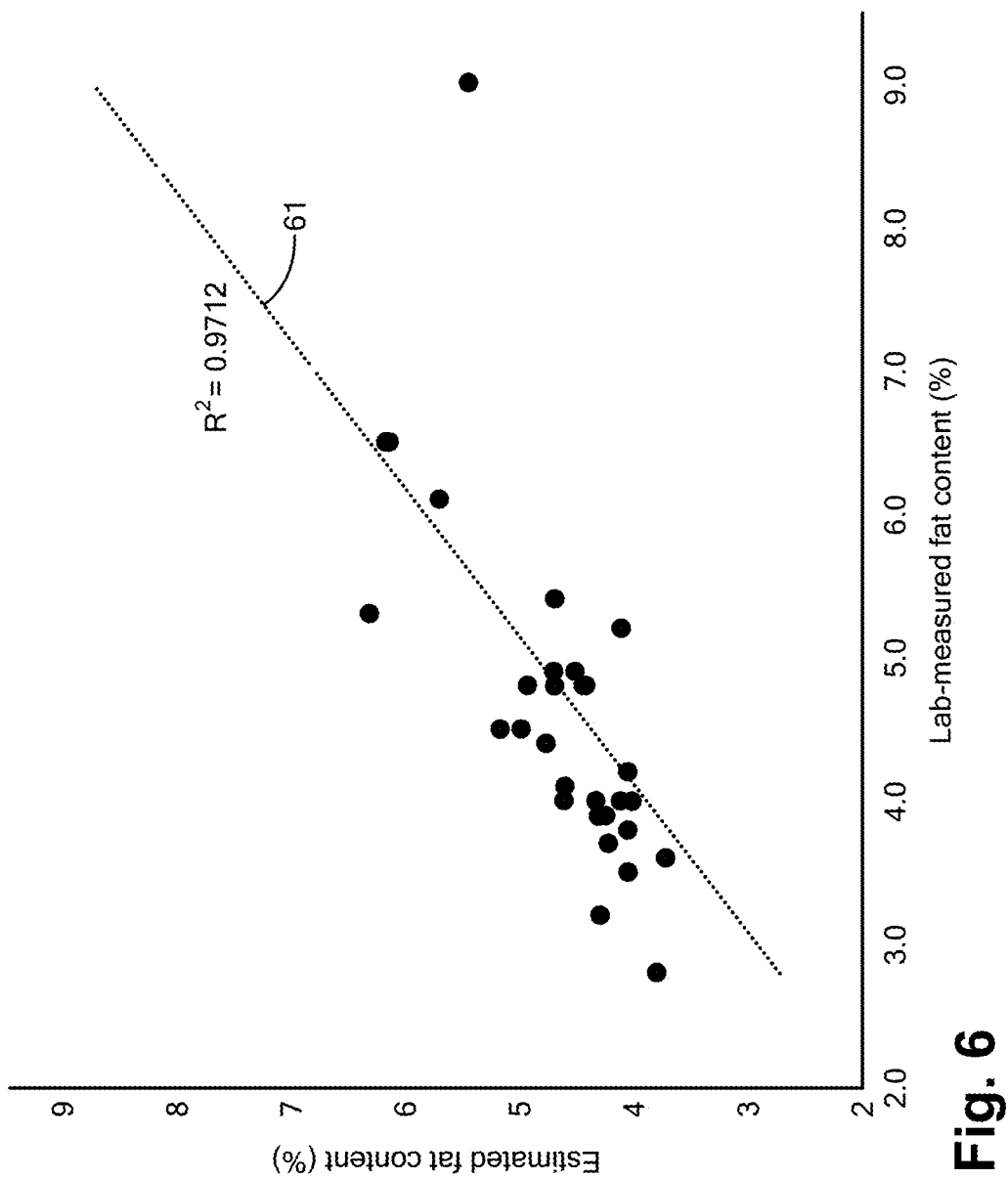
FIG. 6 is a scatter-plot graph plotting fat content (estimated using the processes of FIG. 5) against lab-measured fat content in accordance with an embodiment of the present invention.

FIG. 6 is a scatter-plot graph plotting fat content (estimated using the processes of FIG. 5) against lab-measured fat content in accordance with an embodiment of the present invention. Line 61 represents straight line fit to the fat concentration data. As can be seen from this graph, the estimated fat content provides a good match for the lab measured fat content. The approach demonstrated here for fat content has been demonstrated to work well for protein content and somatic cell count (SCC).

Figure 7:
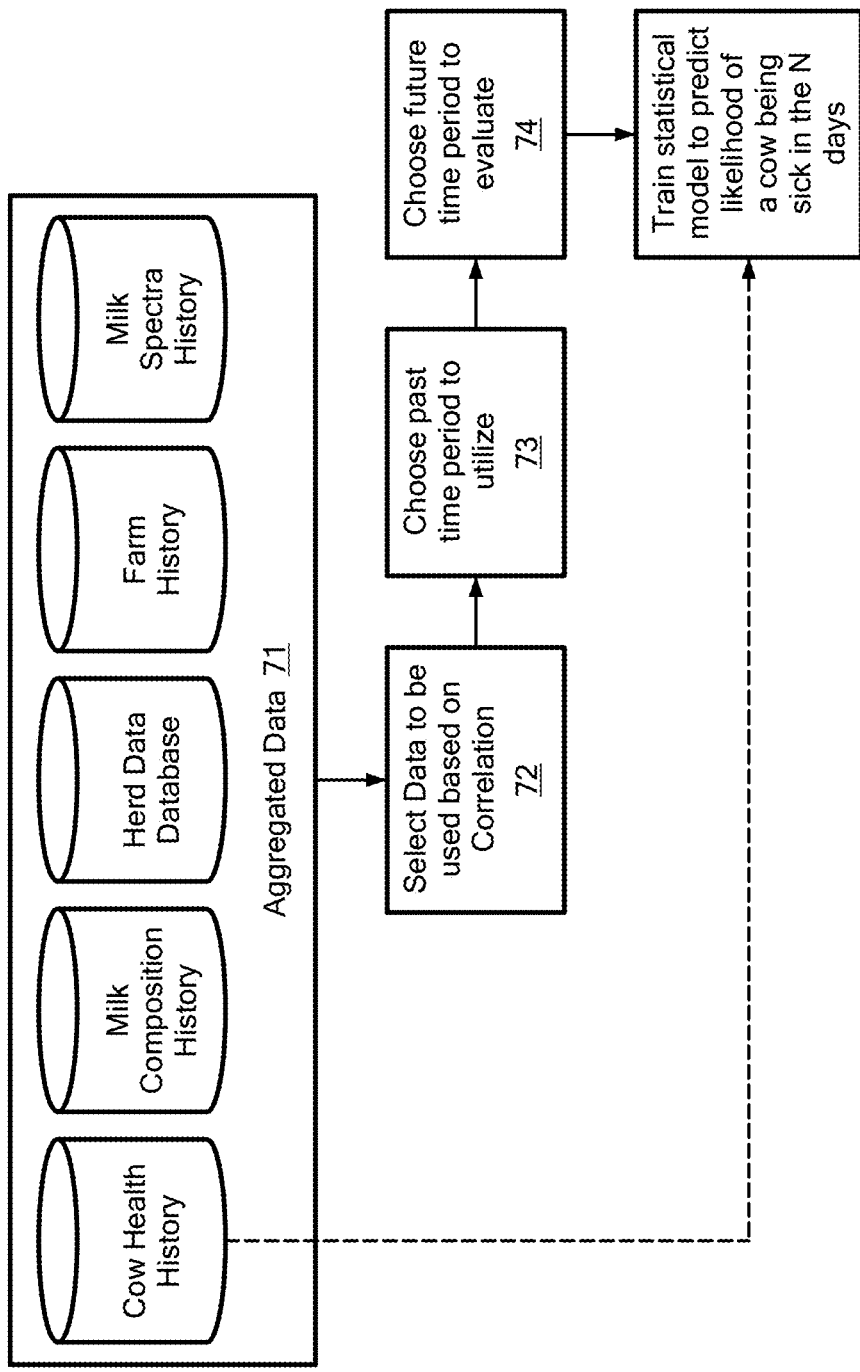
FIG. 7 is a flow diagram showing processes by which a model is trained on aggregated data to predict a cow's future health status in accordance with an embodiment of the present invention.

FIG. 7 is a flow diagram showing processes by which a model is trained on aggregated data to predict a cow's future health status and future milk yield in accordance with an embodiment of the present invention. In process 71, various kinds of data relating to a cow's milking and health history are collected and stored, relating to parameters selected from the group consisting of genetic data and historical time series data, including milk yield, milk composition, days in milk, lactation stage, number of lactations, feed formula, geographic and weather. In process 72, data are retrieved and selected based on correlation with a cow's health status and milk yield. In process 73, a past time range is selected based on correlation with the cow's health and milk yield. In process 74, a future time period is chosen, as the query period for prediction. In process 74, a model is trained following process 56 and process 57 to predict the future milk yield and future health status in a given query period. For example, these processes can be used to predict the likelihood that a given cow will develop mastitis. See also FIGS. 19 and 22 respectively, and accompanying text herein, for a discussion of database structure for storing and augmenting cow, milk and farm data and for a table showing data relevant to such prediction.

Figure 8A:
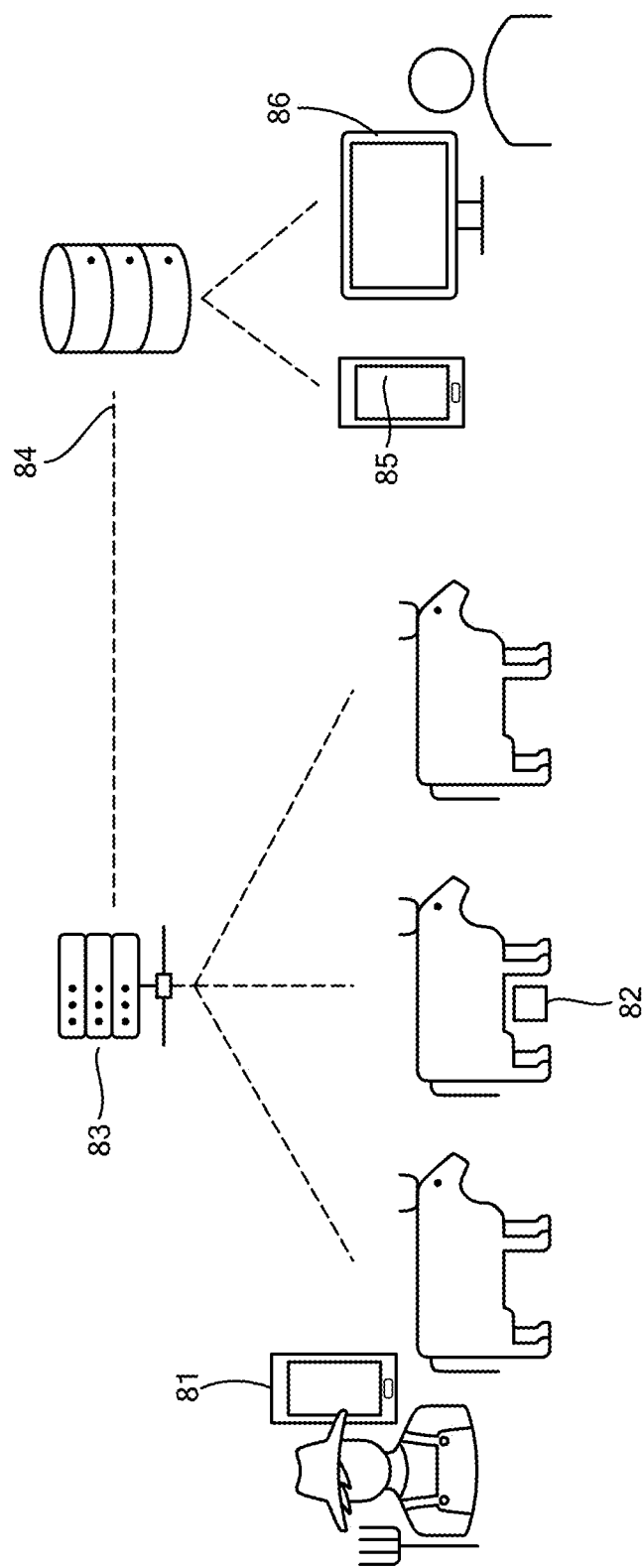
FIG. 8A is a system architecture diagram illustrating components, of a system, supporting on-farm and remote interactions for milk quality testing in accordance with an embodiment of the present invention.

FIG. 8A is a system architecture diagram illustrating components of a system, supporting on-farm and remote interactions for milk quality testing in accordance with an embodiment of the present invention. A user can use a portable device 81 to test collected milk samples. A cow is milked at a milking station, where an inline device 82 takes spectral measurements of milk samples. A server system 83, receives spectral measurements recorded from devices 81 and 82, and estimates the composition of the milk through processes described in connection with FIG. 3 and FIG. 2. The composition estimates are stored in a database 84. The composition information can be viewed on a smartphone application 85 or on a web browser 86.

Figure 8B:
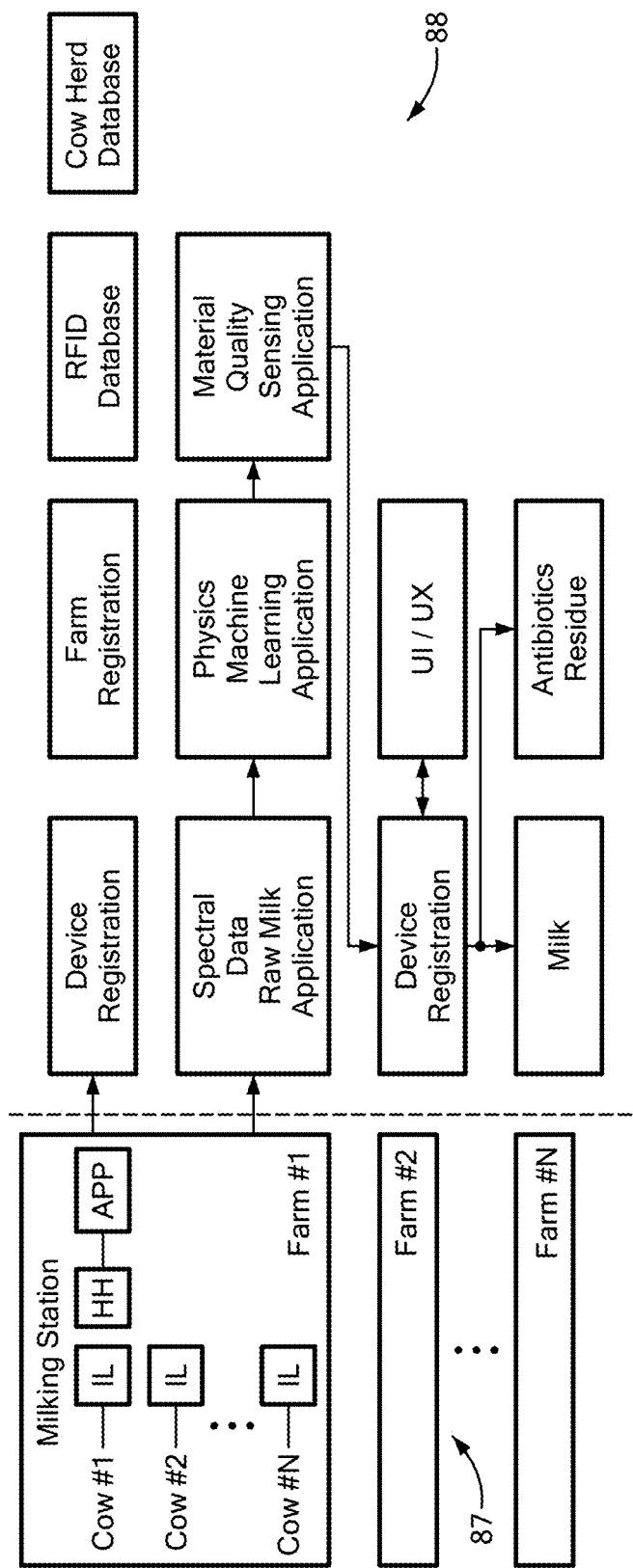
FIG. 8B is a diagram showing, in more detail, the components of the system of FIG. 8A in accordance with an embodiment of the present invention.

FIG. 8B is a diagram showing, in more detail, the components of the system of FIG. 8A in accordance with an embodiment of the present invention. On a farm 87, one or more milking stations are connected to inline testing devices. Spectral measurements are transmitted to a server system, having components 88, which processes the spectral data to estimate milk attributes such as composition. The server system also includes several databases to register and ascribe testing results to specific cows.

Figure 9:
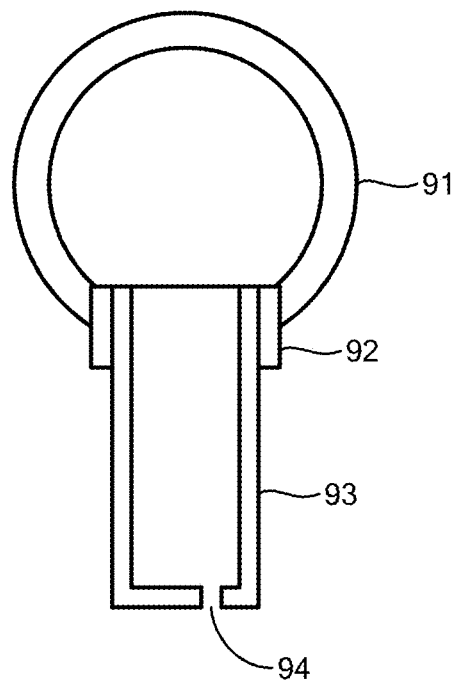
FIG. 9 is a longitudinal section of a sampling cuvette in accordance with an embodiment of the present invention.

FIG. 9 is a longitudinal section of a cuvette assembly in accordance with an embodiment of the present invention. The cuvette assembly includes a flexible bulb 91, a connector attachment 92 and an optically clear cuvette 93. When the bulb is squeezed in a vial containing a milk sample, a volume of milk is drawn into the cuvette assembly through the orifice 94.

Figure 10:
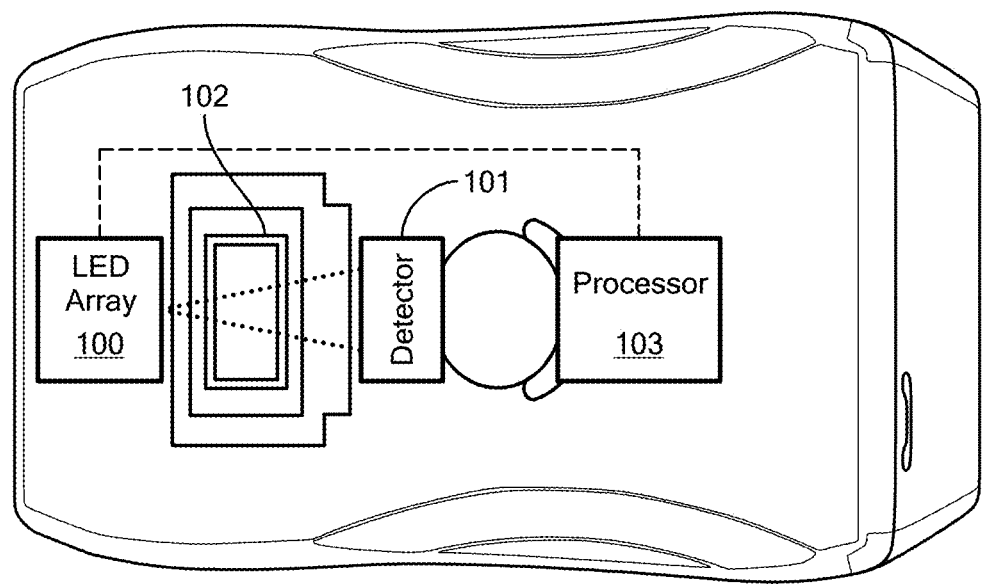
FIG. 10 is a schematic depiction of a hand-held spectroscopic system for milk testing in accordance with an embodiment of the present invention.

FIG. 10 is a schematic depiction of a hand-held device for milk testing in accordance with an embodiment of the present invention. The hand-held device includes an array of light sources 100 that is used to illuminate a milk sample, a slot 102 where a cuvette assembly holding the milk sample can be inserted, a spectrometer 101 that records the spectrum, and a microprocessor 103 that transmits the data to a server system. The hand-held device shown in FIG. 10 is an embodiment of the fluid analyzer presented in FIG. 1.

Figure 11:
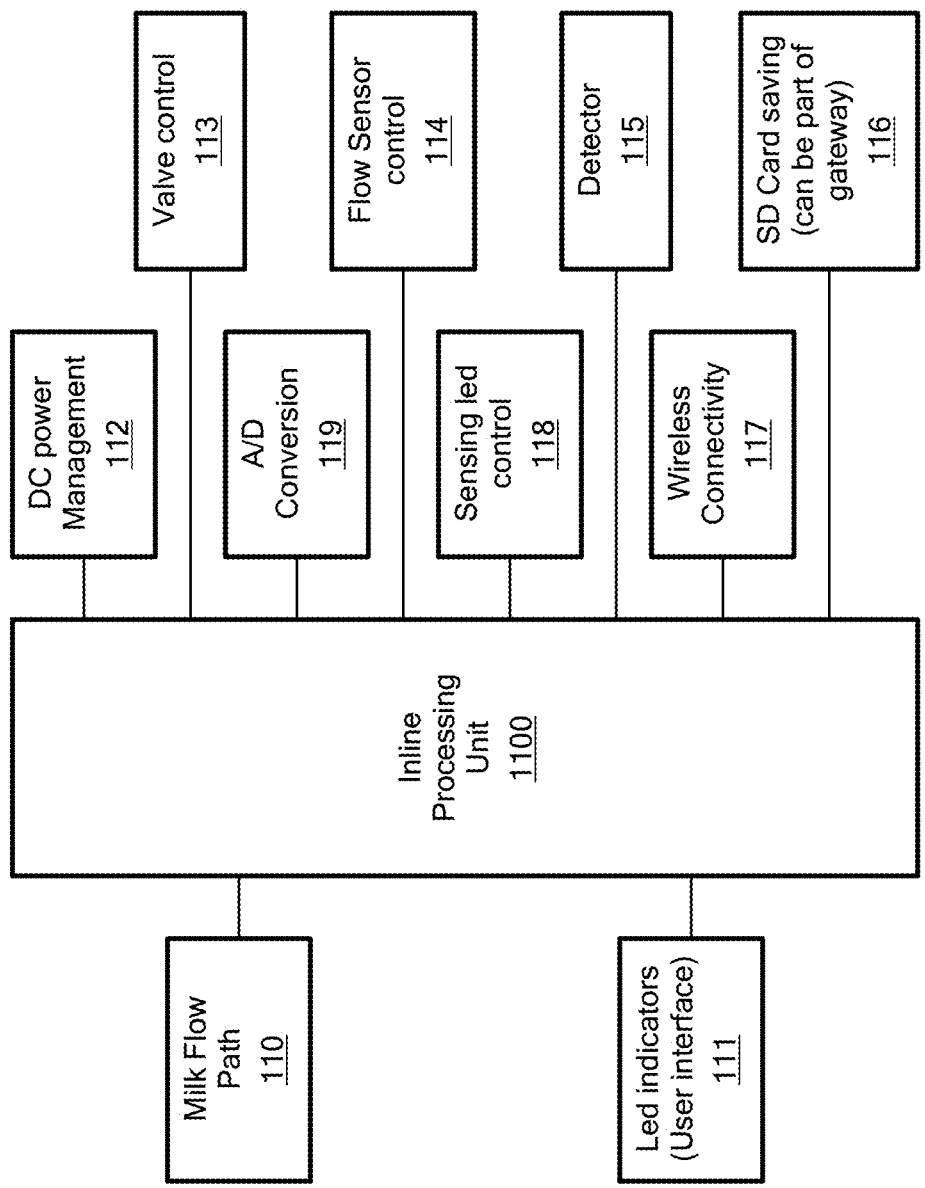
FIG. 11 is a block diagram of major components of a inline spectroscopic system for milk testing in accordance with an embodiment of the present invention.

FIG. 11 is a block diagram of major components of an inline spectroscopic system for milk testing in accordance with an embodiment of the present invention. This inline spectroscopic milk testing system represents one particular embodiment of FIG. 10. This system includes a milk flow path 110 that delivers milk to the detector 115. When the system is powered by the power management circuits 112, power and status indicator lights 111 show the status of connectivity. Once the milk sample enters the milk flow path 110, flow sensor circuits 114 detect the flow and send a trigger to the control circuit for sensing LED sources 118 and to the detector 115 to make a spectral measurement. The analog spectral measurement is converted to a digital signal by the analog-to-digital converter 119, and the digital signal is sent to a server system by the wireless connectivity 117.

Once the measurement is completed, valves 113 control the flow of the milk sample to drain. The detector 115 includes the spectrometer 101 of FIG. 10. This system also includes a local data storage unit 116 that can store spectral data in the event of network disruption.

Figure 12:
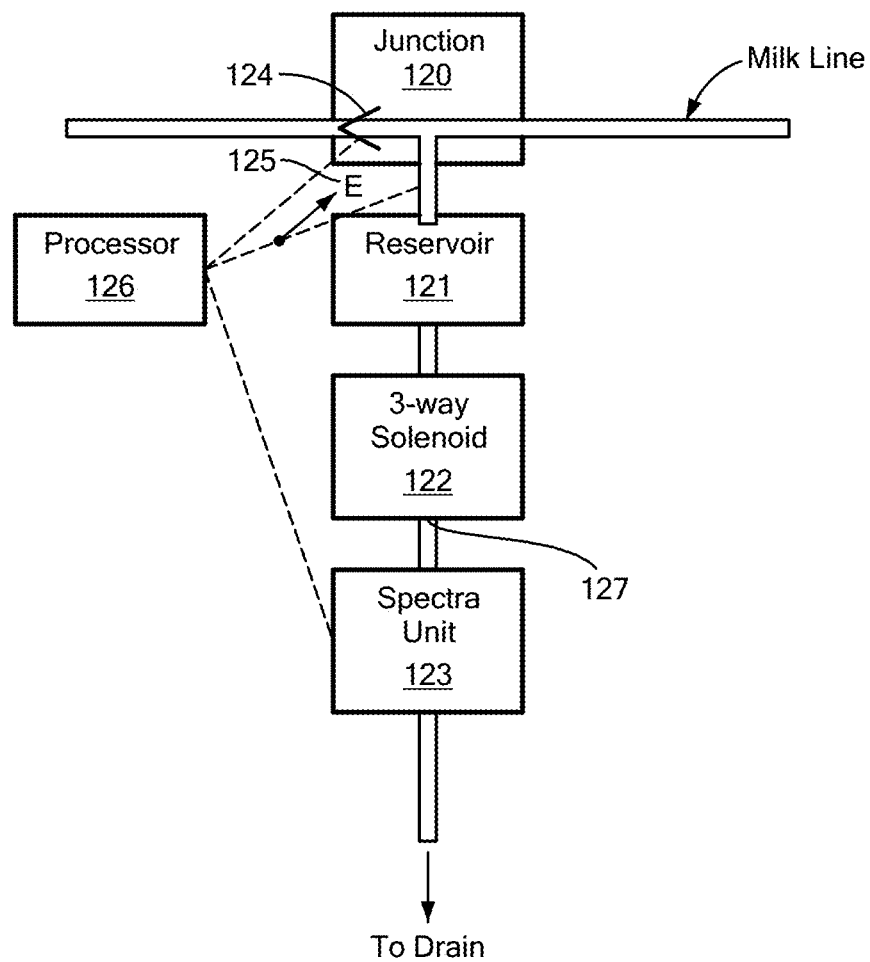
FIG. 12 is a block diagram of an inline milk testing system with embedded sampler and meter in accordance with an embodiment of the present invention.

FIG. 12 is a block diagram of an inline milk testing system with embedded sampler and meter in accordance with an embodiment of the present invention. This system includes a milk line that delivers milk from a milking machine. The milk line is connected to a reservoir 120 that diverts a small representative proportion of milk to a calibrated vial 121 capable of measuring the total yield of milk for a cow. The rest of the milk is sent to a bulk tank using the outlet tube 124. Subsequent to the milking, the flow sensor 125 activates a release of the milk sample from vial 121 through a valve 122 to the inline milk testing unit 123. The milk sample is tested and the spectral measurements are processed by the microprocessor 127 and sent to a server system. The tested milk sample is then released to a drain using the outlet tube 127.

Figure 13:
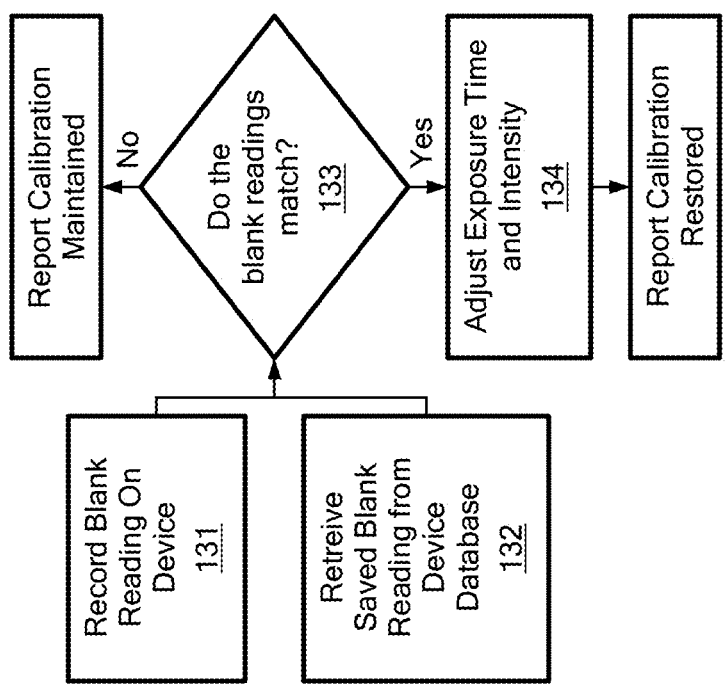
FIG. 13 is a block diagram showing processes by which the calibration on a milk testing device is maintained in accordance with an embodiment of the present invention.

FIG. 13 is a block diagram showing processes by which the calibration of a milk testing device is maintained in accordance with an embodiment of the present invention. In process 131, a blank measurement (namely, a measurement in the absence of a milk sample) is made by a device. In process 132, a previously recorded blank measurement performed on the same device is retrieved from a database. In process 133, the two measurements are compared. If the measurements from 131 and 132 are identical, the milk testing device is determined to remain calibrated. If the measurements are nonidentical, the intensity of light sources or the exposure time of the spectrometer are adjusted to match the measurement in process 132, thereby restoring the calibration.

Figure 14:
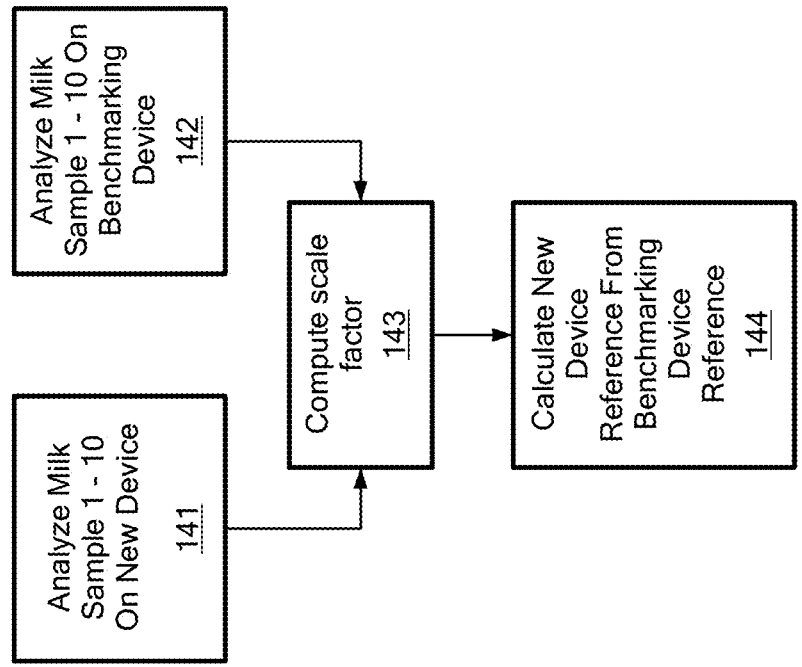
FIG. 14 is a block diagram showing processes by which a new device is calibrated to align with a benchmarking device in accordance with an embodiment of the present invention.

FIG. 14 is a block diagram showing processes by which a new device is calibrated to align with a benchmarking device in accordance with an embodiment of the present invention. In process 141, a set of 10 milk samples is analyzed on a new device. In process 142 the same set of 10 milk samples is analyzed on a benchmarking device. In process 143, the pair of spectral measurements of each sample is divided, and the resulting quotients are averaged, creating a scale factor. In process 144, the scale factor is multiplied by the benchmarking device reference, to obtain a reference for the new device.

Figure 15:
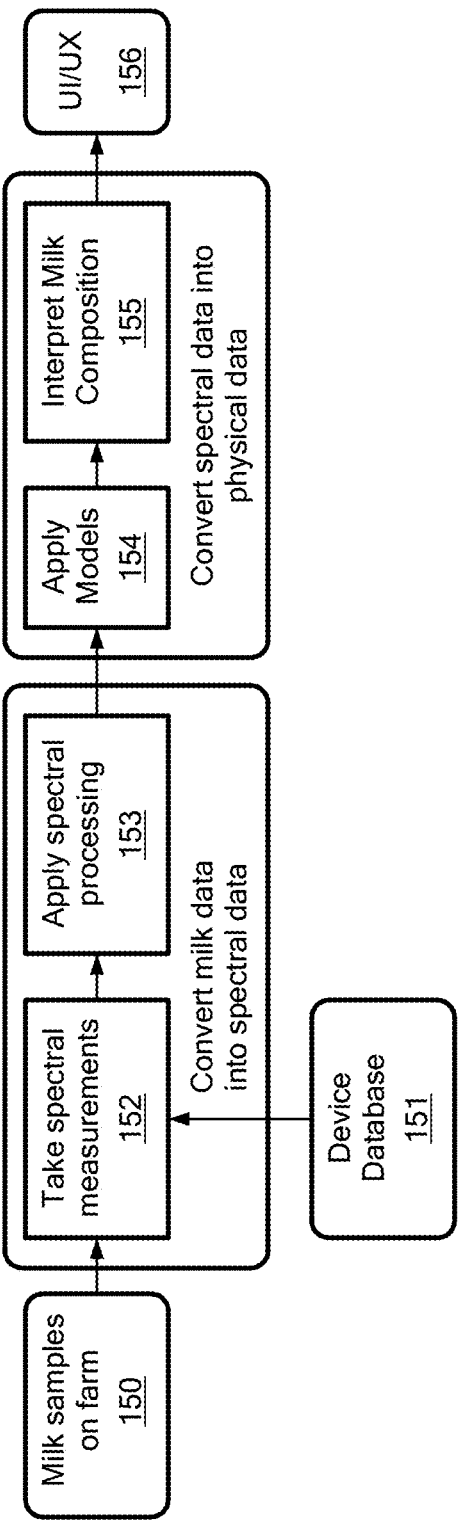
FIG. 15 is a block diagram of processes by which milk is analyzed using spectral measurements, to determine composition in accordance with an embodiment of the present invention.

FIG. 15 is a block diagram of processes by which milk is analyzed using spectral measurements, to determine composition in accordance with an embodiment of the present invention. In process 150, milk samples are collected on a farm. In process 152, spectral measurements are taken of the milk sample. In process 151, calibration data about the testing device are retrieved from a database. In process 153, spectral processing is applied to the recorded spectral measurements using processes described in connection with FIG. 4. In process 154, trained machine learning models are used on the processed spectral data using processes described in connection with FIG. 5. In process 155, the compositional estimates of the milk sample are analyzed. This analysis can be in the form of a comparison to a farm average, or the weekly average of the cow. In process 156, the results of the analysis are presented to a user.

Figure 16:
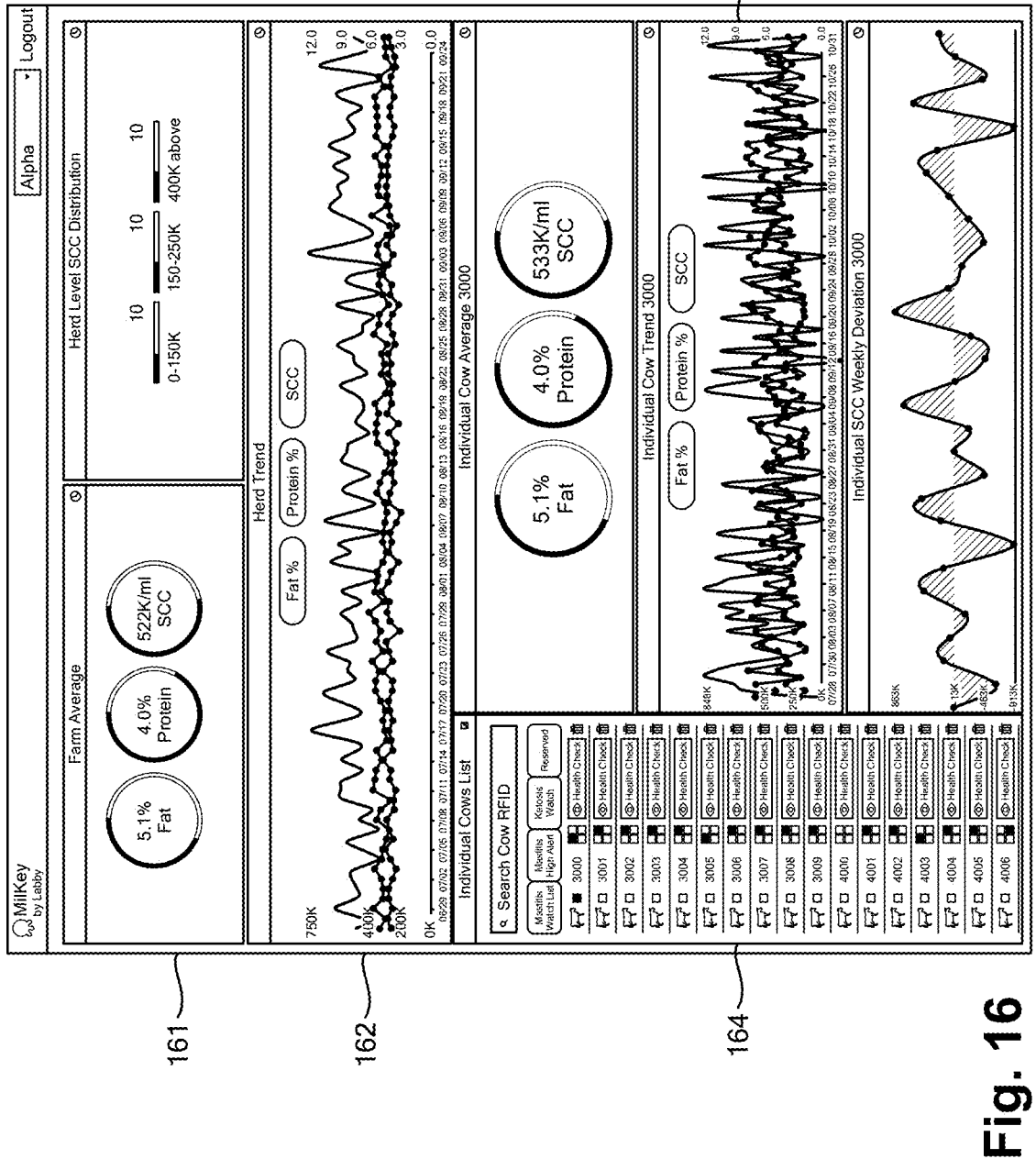
FIG. 16 is a representation of a webpage presenting information in a web analytics portal where farm-level information on milk composition and herd health can be assessed in accordance with an embodiment of the present invention.

FIG. 16 is a representation of a webpage presenting information in a web analytics portal where herd-level information on milk composition and herd health can be assessed in accordance with an embodiment of the present invention. The webpage section 161 displays the herd-level milk composition information of the current day. The webpage section 162 illustrates the average herd-level milk composition information over a selected time period chosen by a user. In webpage section 163, the recent milk composition results, milk composition history, and the somatic cell count history of a user-selected cow are displayed. The webpage section 164 summarizes the distribution of the milk somatic cell count information in a herd.

Figure 17D:
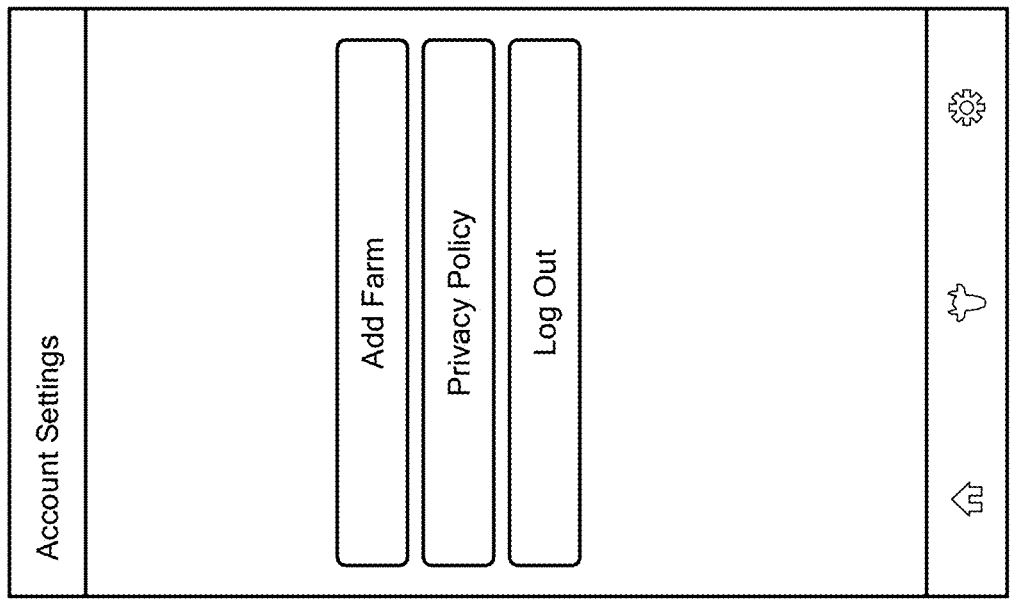
Figure 17C:
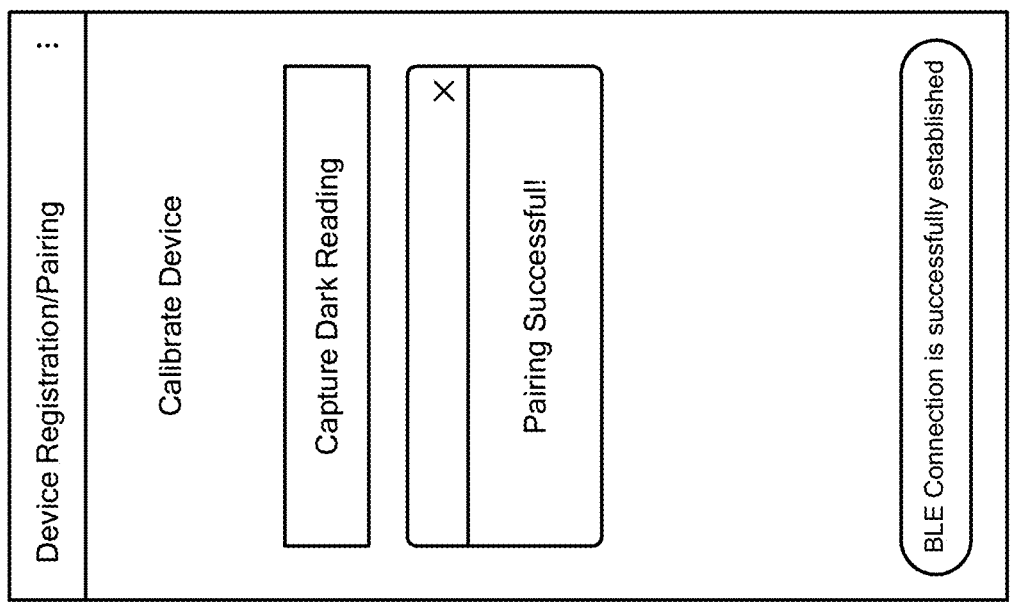
Figure 17H:
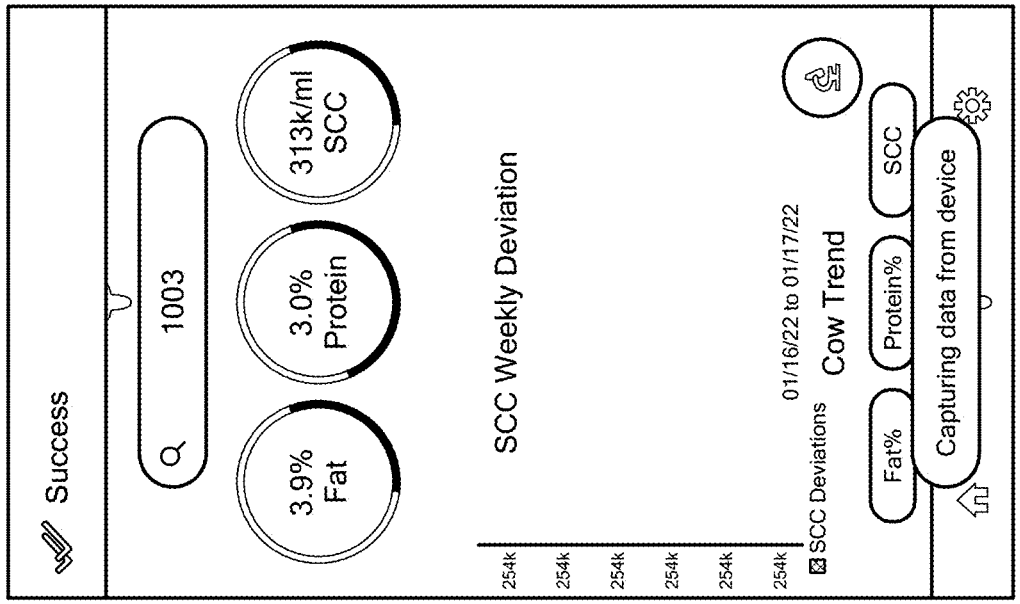
Figure 17G:
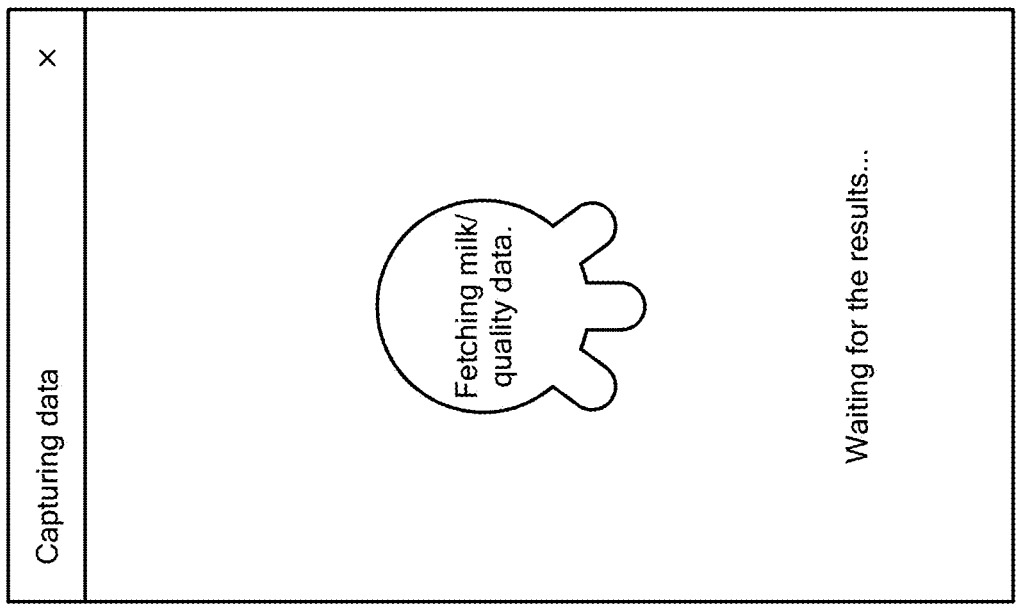
Figure 17I:
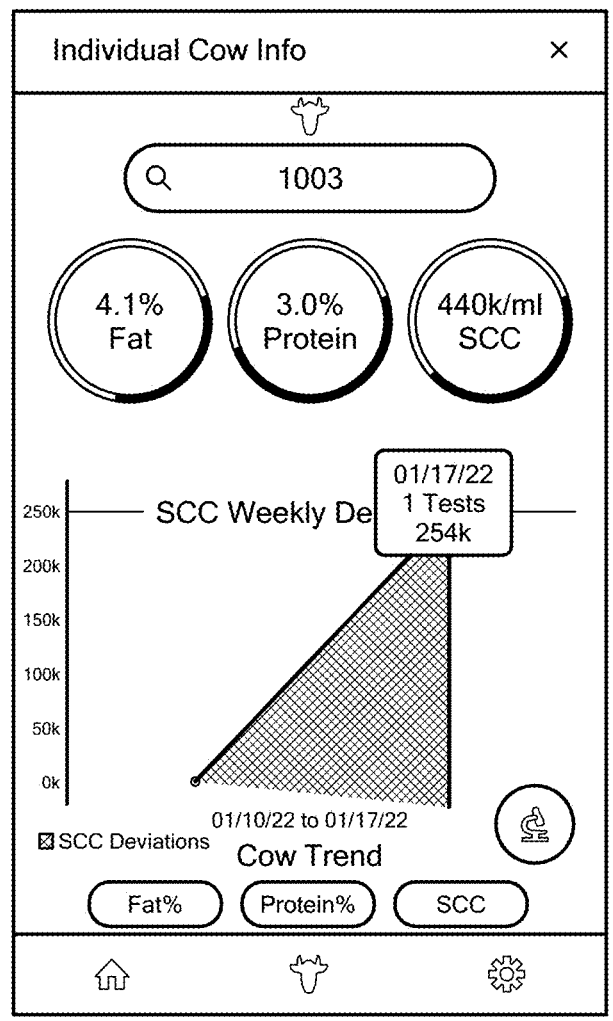

FIG. 17A through FIG. 17I are representations of successive displays in a smartphone application showing how a user can initiate milk testing on a handheld device and evaluate a single cow or a total farm's performance in accordance with an embodiment of the present invention. FIG. 17A is the representation of the device configuration and account management features; FIG. 17B is the representation of a list of devices owned by a user; FIG. 17C represents the process by which devices successfully connect to the smartphone application; FIG. 17D is the representation of account settings, including the addition of new farms; FIG. 17E illustrates a variation of groups of cows with milk information organized and tagged by varied metrics; FIG. 17F displays a variety of information associated with specific cows of interest; FIG. 17G represents device prompts while a user is waiting for the milk testing results of milk testing performed on the fluid analyzer of FIG. 1; FIG. 17H represents the information a user receives from a successful milk testing from the fluid analyzer of FIG. 1; FIG. 17I, in a manner similar to FIG. 17F, displays alternative information associated with a specific cow of interest.

Figure 18:
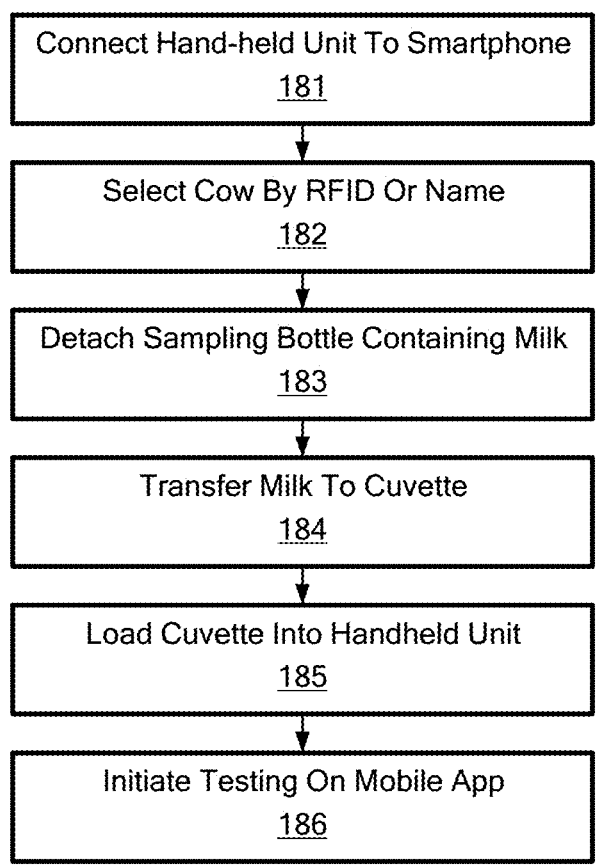
FIG. 18 is block diagram showing processes by which a user can analyze a milk sample using a handheld unit in accordance with an embodiment of the present invention.

FIG. 18 is a block diagram showing processes by which a user can analyze a milk sample using a handheld unit in accordance with an embodiment of the present invention. In process 181, a hand-held fluid analyzer is connected with a smartphone application through a Bluetooth connection. In process 182, a user selects a cow by its RFID number or name, on the smartphone application, from a list of cows, as depicted in FIG. 17E. In process 183, a sampling bottle containing milk from the selected cow is detached from the milk line. In process 183, a cuvette assembly is used to collect a portion of the milk. In process 184, the cuvette assembly containing the milk is loaded into the handheld unit. In process 186, a user initiates the testing on the smartphone application, as detailed in FIG. 17E through FIG. 17I.

Figure 19:
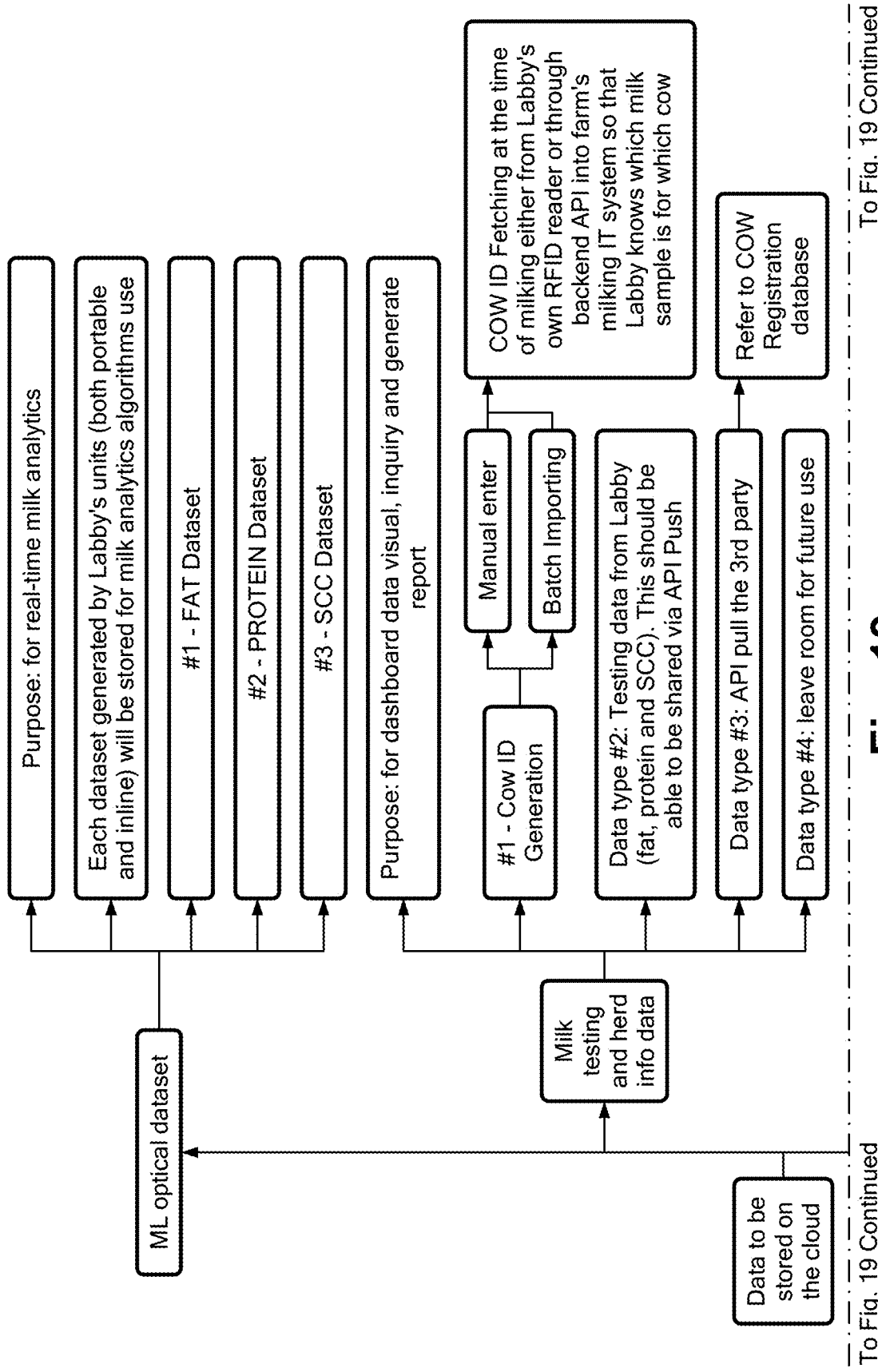
FIG. 19 is a diagram of a database structure for storing cow, milk and farm data, for access and sharing in accordance with an embodiment of the present invention.
Figure 19:
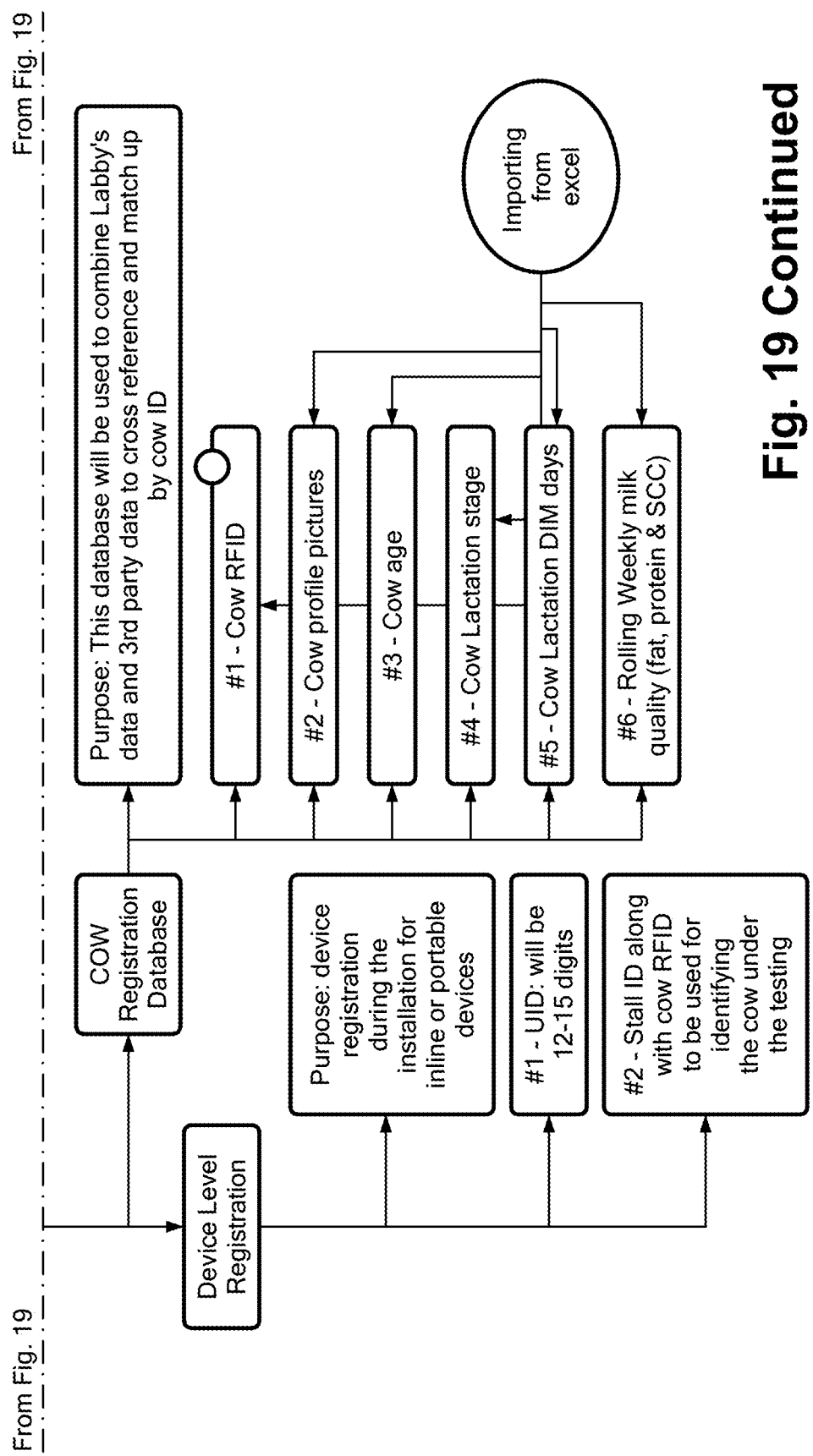

FIG. 19 is a diagram of a database structure for storing and augmenting cow, milk and farm data, for access and sharing in accordance with an embodiment of the present invention. On the left-hand side of the figure appear data to be stored in the server system (cloud). These data are grouped into four categories: machine learning optical dataset, milk testing and herd information data, cow registration database, and device level registration information. The machine learning optical dataset in turn, has parts that include data for analysis of fat, data for analysis of protein and data for analysis of somatic cell count. The milk testing and herd information data includes cow identification generation, milk composition estimates from machine learning models, and additional data obtained from 3rd party sources. The cow registration database includes cow radio frequency identification, cow profile pictures, cow age, cow lactation stage, cow lactation days-in-milk, and weekly average milk composition. Device level registration includes unique identification and stall identification. (See also FIG. 7 and accompanying text for discussion of development of health status information for each cow.)

Figure 20B:
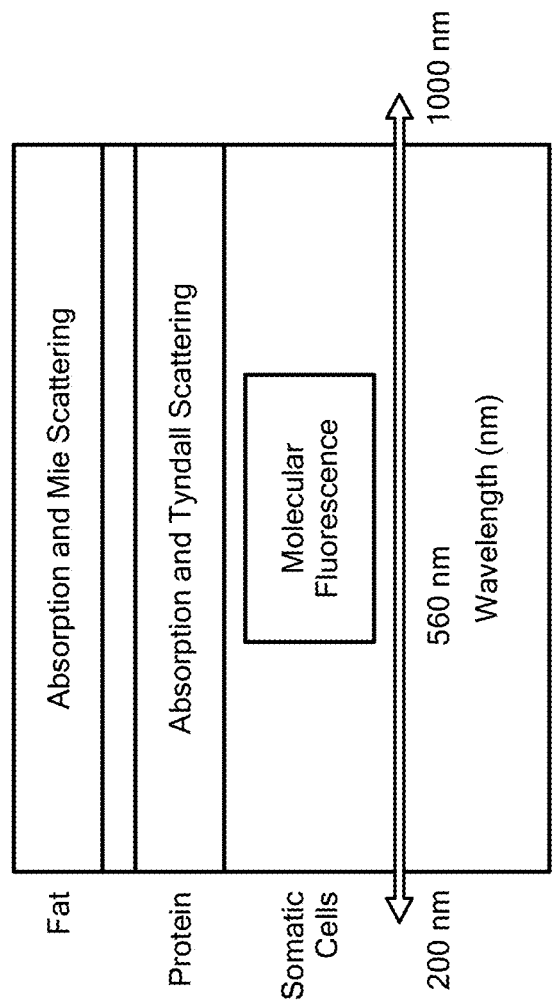
FIG. 20B is a diagram showing light interactions with identified components, in identified spectral regions, in accordance with an embodiment of the present invention.
Figure 20A:
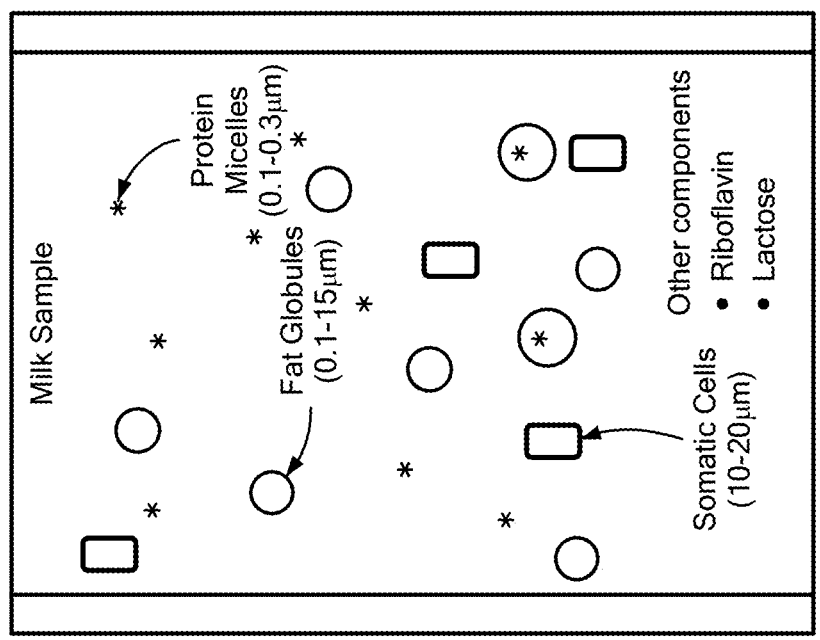
FIG. 20A is a diagram of components of milk that can be detected by spectral analysis in accordance with an embodiment of the present invention.

FIG. 20A is a diagram of components of milk that can be detected by spectral analysis in accordance with an embodiment of the present invention. These components include fat globules, protein micelles, and somatic cells. Optionally, other components include riboflavin and lactose.

FIG. 20B is a diagram showing light interactions with identified components (including fat, protein and somatic cells), in identified spectral regions, in accordance with an embodiment of the present invention.

Figures 21A, 21B:
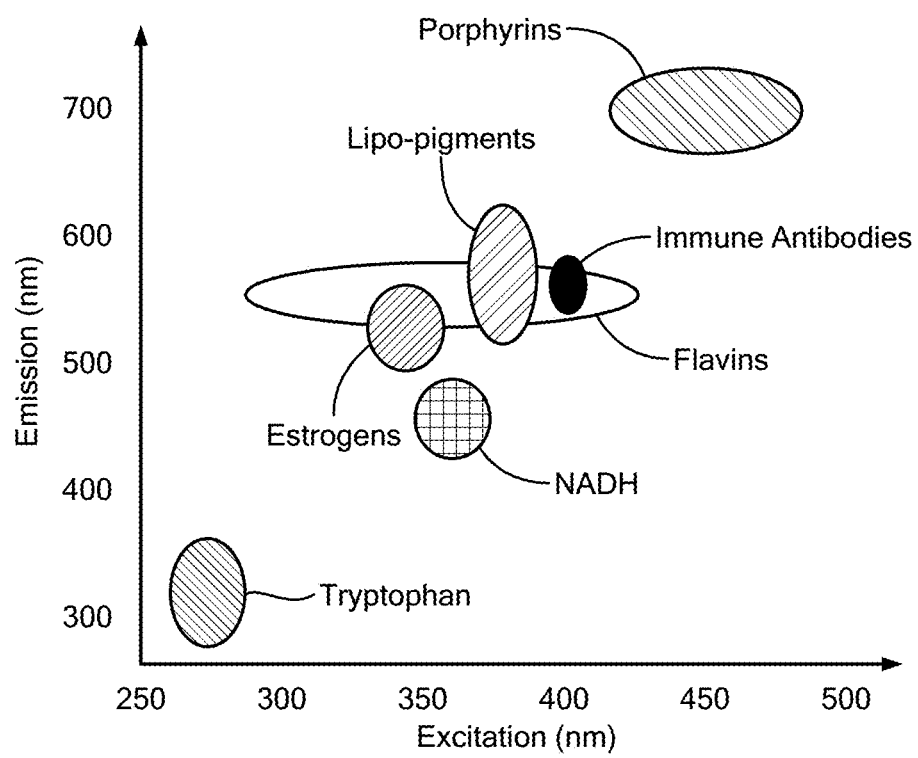
FIG. 21A is a table of representative fluorescent biomarker molecules present in milk, their exemplary excitation and emission principal wavelengths, and the target analytes in milk that can be estimated from fluorescence of these biomarkers, in accordance with an embodiment of the present invention.
FIG. 21B is a graph, plotting, for various of the biomarker molecules listed in FIG. 21A, their exemplary excitation and emission principal wavelengths.

FIG. 21A is a table of representative fluorescent biomarker molecules present in milk, their exemplary excitation and emission principal wavelengths, and the target analytes in milk that can be estimated from fluorescence of these biomarkers, in accordance with an embodiment of the present invention. By measuring the fluorescence spectral response of one or more of these biomarker molecules to its corresponding excitation wavelength, listed in the table, a trained machine learning system can estimate the composition of the corresponding target analyte, as a result of a correlation between fluorescence of the biomarker molecule and its corresponding target analyte.

FIG. 21B is a graph, plotting, for several of the biomarker molecules listed in FIG. 21A, their exemplary excitation and emission principal wavelengths.

Figure 22:
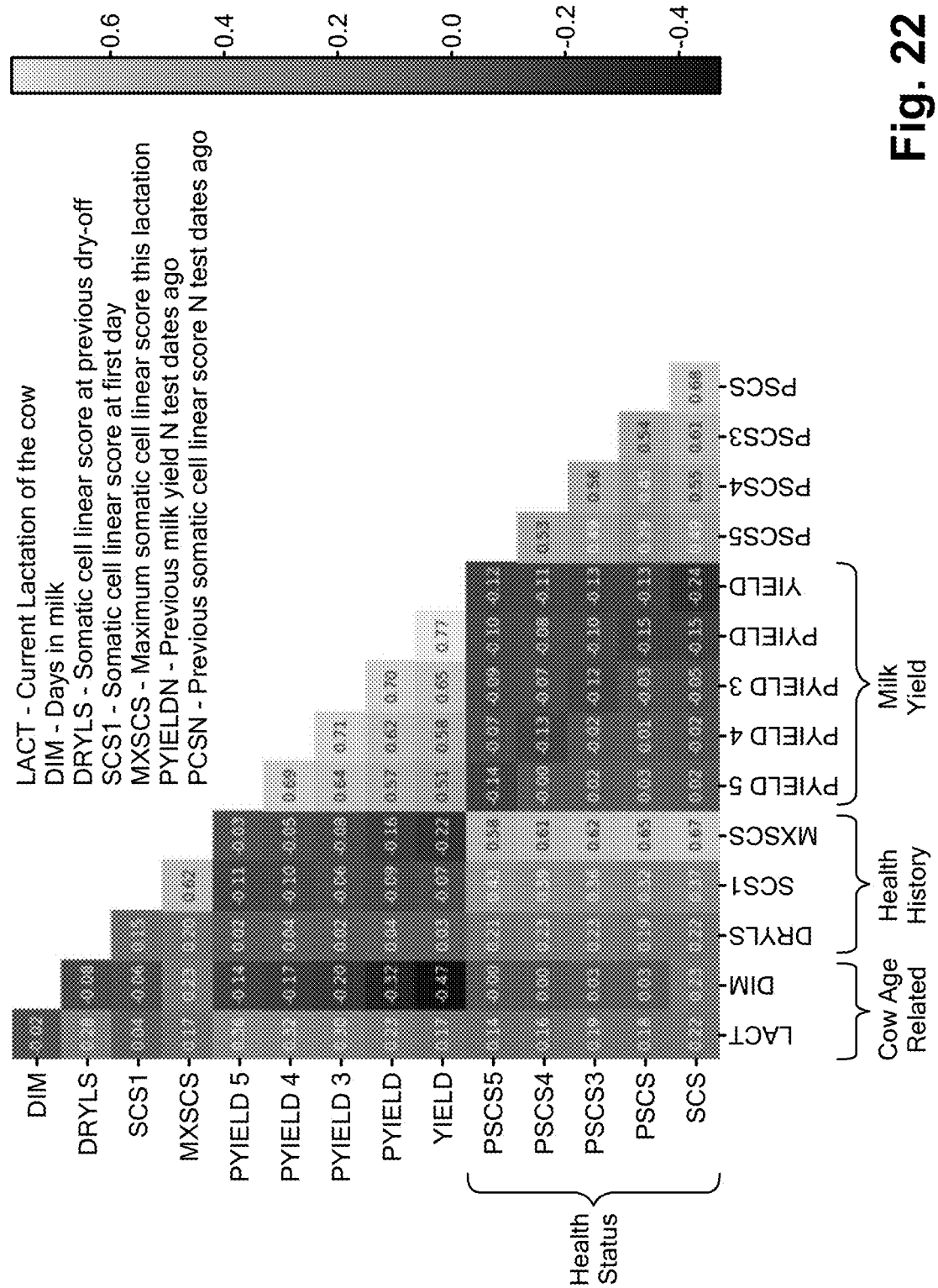
FIG. 22 is a diagram showing the correlation of milking data from a set of farms over several months with respect to parameters indicative of health status, cow age-related items, health history, and milk yield.

FIG. 22 is a table showing the correlation of milking data from a set of farms over several months with respect to parameters indicative of health status, cow age-related items, health history, and milk production. The table illustrates relationships among these various parameters that can be used by a trained machine learning model to estimate future health status and future milk yield.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method of analyzing milk, the method using processes comprising:
  obtaining a milk sample from a cow, the cow coupled to an inline milking system, by which milk is pumped in a milk line from the cow to a bulk tank for later distribution, in a manner wherein the milk sample is extracted in a discrete flow path of the inline milking system;
  causing irradiation of the sample with light in a plurality of discrete spectral bands lying in a range from near-infrared through ultraviolet to cause production of a fluorescence response, wherein each discrete spectral band is selected on the basis of a fluorescence phenomenon of a corresponding analyte of interest;
  receiving, from an analog to digital converter coupled to a set of light sensors, digitized spectral data that includes first data characterizing the fluorescence response; and
  transmitting the digitized spectral data to a machine learning system, the system trained on data selected from the group consisting of cow health history, milk composition history, herd data, farm history, milk spectra history, and combinations thereof to (a) determine concentration in the sample of a set of analytes selected from the group consisting of somatic cells, fat, protein, lactose, antibiotics, pathogens, hormones, and combinations thereof; (b) produce a concentration data output; and (c) predict a set of physiological parameters of the cow.

2. A method according to claim 1, wherein causing irradiation of the sample includes causing irradiation of the sample sequentially in each one of the plurality of discrete spectral bands.

3. A method according to claim 1, wherein the discrete spectral band selected for the corresponding one of the analytes is a discrete spectral band selected on the basis of the fluorescence phenomenon of a biomarker identified as a proxy for the corresponding one of the analytes.

4. A method according to claim 3, wherein the corresponding one of the analytes is cells and the identified biomarker is immune antibodies, for which the irradiation is caused in a spectral band including 410 nm and the fluorescence response is in a spectral band at 570 nm.

5. A method according to claim 3, wherein the corresponding one of the analytes is cells and the identified biomarker is nicotinamide adenine dinucleotide, for which the irradiation is caused in a spectral band including 340 nm and the fluorescence response is in a spectral band including 450 nm.

6. A method according to claim 3, wherein the corresponding one of the analytes is cells and the identified biomarker is lipo-pigments, for which the irradiation is caused in a spectral band including 350 nm and the fluorescence response is in a spectral band including 600 nm.

7. A method according to claim 3, wherein the corresponding one of the analytes is fat and the identified biomarker is flavins, for which the irradiation is caused in a spectral band including 450 nm and the fluorescence response is in a spectral band including 550 nm.

8. A method according to claim 3, wherein the corresponding one of the analytes is cells and the identified biomarker is lacto-ferrin, for which the irradiation is caused in a spectral band including 450 nm and the fluorescence response is in a spectral band including 560 nm.

9. A method according to claim 3, wherein the corresponding one of the analytes is selected from the group consisting of blood, cells, chlorophyll and combinations thereof and the identified biomarker is porphyrins, for which the irradiation is caused in a spectral band including 410 nm and the fluorescence response is in a spectral band including 630 nm.

10. A method according to claim 3, wherein the corresponding one of the analytes is hormones and the identified biomarker is estrogens, for which the irradiation is caused in a spectral band including 350 nm and the fluorescence response is in a spectral band including 530 nm.

11. A method according to claim 3, wherein the corresponding one of the analytes is selected from the group consisting of protein and lactose and the identified biomarker is tryptophan, for which the irradiation is caused in a spectral band including 280 nm and the fluorescence response is in a spectral band including 330 nm.

12. A method according to claim 1, wherein causing irradiation of the sample further includes causing irradiation to cause production of a transmitted light response and the digitized spectral data include second data characterizing the transmitted light response.

13. A method according to claim 1, wherein the set of physiological parameters includes the cow's future health status.

14. A method according to claim 1, wherein the set of physiological parameters includes the cow's future milk yield.

15. A method according of claim 1, wherein the machine learning system is further trained on data selected from the group consisting of milk yield, milk composition, days in milk, lactation stage, number of lactations, and feed formula.

16. An inline milking system for analyzing a milk sample, the system comprising:
- an in-line receptacle configured to receive the milk sample from a discrete flow path of the inline milking system, by which milk is pumped in a milk line from the cow to a bulk tank for later distribution;
- a light source configured to irradiate the sample in a plurality of discrete spectral bands, lying in a range from near-infrared through ultraviolet and selected on the basis of a fluorescence phenomenon of an analyte of interest to cause production of a fluorescence response;
- a light detector and an analog-to-digital converter coupled thereto providing a digitized spectral data output that includes first data characterizing the fluorescence response; and
- a machine learning system coupled to the digitized spectral data output, the machine learning system trained on data selected from the group consisting of cow health history, milk composition history, herd data, farm history, milk spectra history, and combinations thereof to fa) determine concentration in the sample of a set of analytes selected from the group consisting of somatic cells, fat, protein, lactose, antibiotics, hormones, and combinations thereof; (b) produce a concentration data output; and (c) predict a set of physiological parameters of the cow;
- wherein each one of the discrete spectral bands has been selected on the basis of a fluorescence phenomenon of a corresponding one of the analytes.

17. A system according to claim 16, wherein the light source is configured to irradiate the sample sequentially in each one of the plurality of discrete spectral bands.

18. A system according to claim 16, wherein the discrete spectral band selected for the corresponding one of the analytes is a discrete spectral band selected on the basis of a fluorescence phenomenon of a biomarker identified as a proxy for the corresponding one of the analytes.

19. A system according to claim 18, wherein the corresponding one of the analytes is cells and the identified biomarker is immune antibodies, for which the irradiation is caused in a spectral band including 410 nm and the fluorescence response is in a spectral band at 570 nm.

20. A system according to claim 18, wherein the corresponding one of the analytes is cells and the identified biomarker is nicotinamide adenine dinucleotide, for which the irradiation is caused in a spectral band including 340 nm and the fluorescence response is in a spectral band including 450 nm.

21. A system according to claim 18, wherein the corresponding one of the analytes is cells and the identified biomarker is lipo-pigments, for which the irradiation is caused in a spectral band including 350 nm and the fluorescence response is in a spectral band including 600 nm.

22. A system according to claim 18, wherein the corresponding one of the analytes is fat and the identified biomarker is flavins, for which the irradiation is caused in a spectral band including 450 nm and the fluorescence response is in a spectral band including 550 nm.

23. A system according to claim 18, wherein the corresponding one of the analytes is cells and the identified biomarker is lacto-ferrin, for which the irradiation is caused in a spectral band including 450 nm and the fluorescence response is in a spectral band including 560 nm.

24. A system according to claim 18, wherein the corresponding one of the analytes is selected from the group consisting of blood, cells, chlorophyll and combinations thereof and the identified biomarker is porphyrins, for which the irradiation is caused in a spectral band including 410 nm and the fluorescence response is in a spectral band including 630 nm.

25. A system according to claim 18, wherein the corresponding one of the analytes is hormones and the identified biomarker is estrogens, for which the irradiation is caused in a spectral band including 350 nm and the fluorescence response is in a spectral band including 530 nm.

26. A system according to claim 18, wherein the corresponding one of the analytes is selected from the group consisting of protein and lactose and the identified biomarker is tryptophan, for which the irradiation is caused in a spectral band including 280 nm and the fluorescence response is in a spectral band including 330 nm.

27. A system according to claim 16, wherein the light source is further configured to cause production of a transmitted light response and the digitized spectral data include second data characterizing the transmitted light response.

28. A computer-implemented system according to claim 16, wherein the receptacle is configured to receive and analyze the milk sample from the inline milking system.

29. A computer-implemented system according to claim 28, wherein the computer-implemented system is configured to receive and analyze a series of milk samples over a succession of test frames.

* * * * *